United States Patent [19]

Armitage et al.

[11] Patent Number: 5,674,492
[45] Date of Patent: Oct. 7, 1997

[54] METHOD OF PREVENTING OR TREATING DISEASE CHARACTERIZED BY NEOPLASTIC CELLS EXPRESSING CD40

[75] Inventors: Richard J. Armitage, Bainbridge Island; William C. Fanslow, III, Federal Way, both of Wash.; Dan L. Longo, Kensington; William J. Murphy, Frederick, both of Md.

[73] Assignees: Immunex Corporation, Seattle, Wash.; The United States of America as represented by the Department of Health and Human Services, Washington, D.C.

[21] Appl. No.: 360,923

[22] Filed: Dec. 21, 1994

Related U.S. Application Data

[63] Continuation-in-part of Ser. No. 172,664, Dec. 23, 1993, abandoned.

[51] Int. Cl.$^6$ .................. A61K 39/395; A61K 35/12; A61K 38/02
[52] U.S. Cl. .................. 424/144.1; 424/143.1; 424/153.1; 424/154.1; 424/155.1; 424/172.1; 424/173.1; 424/174.1; 514/2; 514/8
[58] Field of Search .................. 424/130.1, 133.1, 424/134.1, 136.1, 138.1, 141.2, 143.1, 144.1, 153.1, 154.1, 155.1, 173.1, 172.1, 174.1; 435/252.3, 320.1; 514/48; 530/350, 351, 388.22, 388.73

[56] References Cited

FOREIGN PATENT DOCUMENTS

WO96/18413  6/1996  WIPO.

OTHER PUBLICATIONS

Heath et al. Cell Immunol. 152: 468–480 (1993).

Warner et al Cell Immunol. 115: 195–203 (1988).

Law Leukemia 4: 732–738 (1990).

Dermer Biotechnology 12: 320 (1994).

Dillman J Clin Oncol. 12: 1497–1535 (1994).

Ferraiolo Plenum Press NY 1992.

*Primary Examiner*—Lila Feisee
*Assistant Examiner*—Phillip Gambel
*Attorney, Agent, or Firm*—Patricia Anne Perkins

[57] ABSTRACT

There is disclosed a method of treating a mammal afflicted with a disease characterized by neoplastic cells that express CD40, comprising administering a therapeutically effective amount of a CD40 binding protein in a pharmaceutically acceptable buffer. CD40 binding proteins include monoclonal antibodies to CD40, and CD40 ligand. CD40 binding proteins may also be used to prevent disease characterized by neoplastic cells that express CD40, in individuals at risk for such disease.

18 Claims, 6 Drawing Sheets

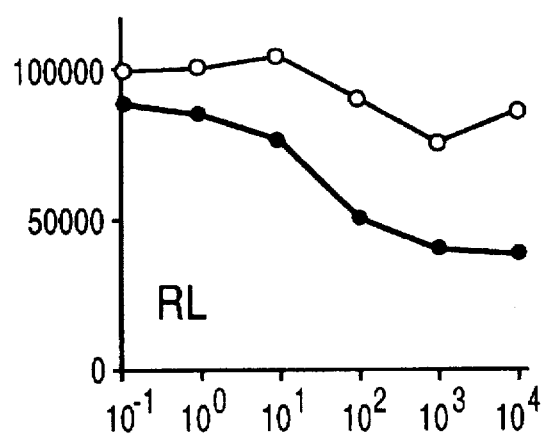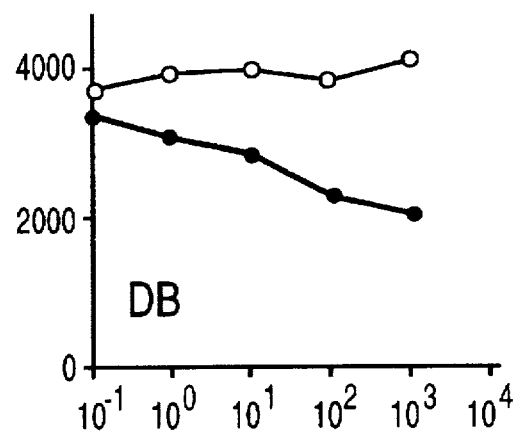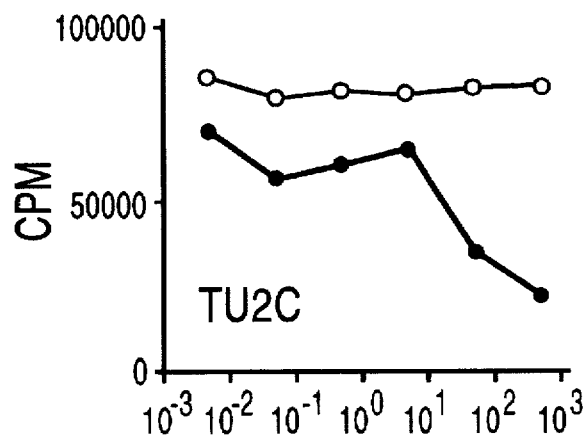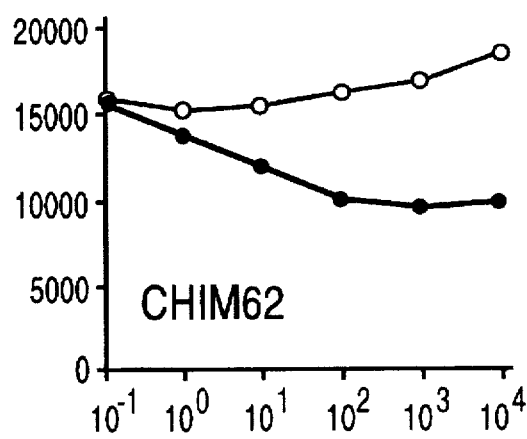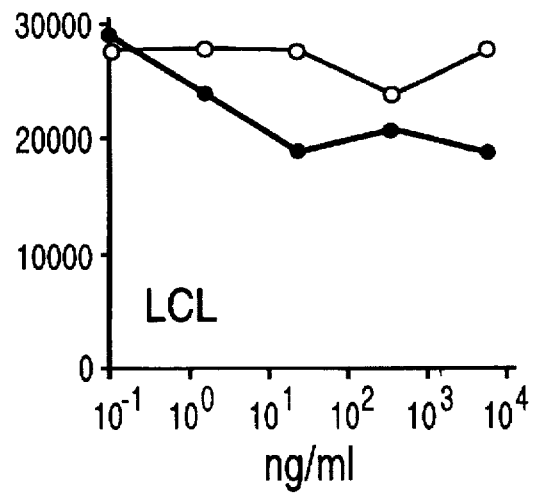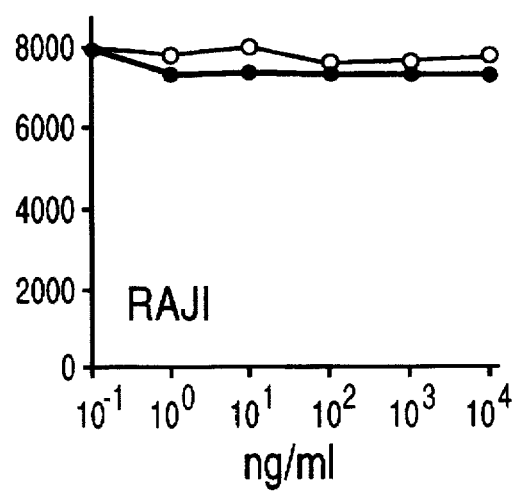

METHOD OF PREVENTING OR TREATING DISEASE CHARACTERIZED BY NEOPLASTIC CELLS EXPRESSING CD40

CROSS-REFERENCE TO RELATED APPLICATION

This application is a continuation-in-part of U.S. application Ser. No. 08/172,664, filed Dec. 23, 1993, now abandoned.

TECHNICAL FIELD OF THE INVENTION

The present invention relates to methods of preventing or treating diseases characterized by neoplastic cells expressing CD40. More specifically, the present invention relates to methods of treating or preventing B-cell lymphomas.

BACKGROUND OF THE INVENTION

Immunoblastic B-cell lymphomas frequently arise in immunocompromised individuals such as allograft recipients and others receiving long-term immunosuppressive therapy, AIDS patients and patients with primary immunodeficiency syndromes such as X-linked lymphoproliferative syndrome or Wiscott-Aldrich syndrome (Thomas et al., *Adv. Cancer Res.* 57:329, 1991; Straus et al., *Ann. Intern. Med.* 118:45, 1993). These tumors appear to arise as a result of impaired T cell control of latent Epstein-Barr virus (EBV) infection. Similar lymphomas of human origin can be induced in mice with severe combined immunodeficiency syndrome (SCID) by inoculation of peripheral blood lymphocytes (PBL) from healthy, EBV-positive individuals (Mosier et al., *Nature* 335:256, 1988; Rowe et al., *J. Exp. Med.* 173:147, 1991).

CD40, a cell-surface antigen present on the surface of both normal and neoplastic human B cells, is a peptide of 277 amino acids having a predicted molecular weight of 30,600, with a 19 amino acid secretory signal peptide comprising predominantly hydrophobic amino acids. This cell surface antigen has been shown to play an important role in B-cell proliferation and differentiation. A cDNA encoding CD40 was isolated from a cDNA library prepared from Burkitt lymphoma cell line Raji (Stamenkovic et al., *EMBO J.* 8:1403, 1989). CD40 is also expressed on the surface of monocytic and epithelial cells, and on some epithelial carcinomas (E. A. Clark, *Tissue Antigens* 36:33; 1990).

Activated CD4+ T cells express high levels of a ligand for CD40 (CD40L). Human CD40L, a membrane-bound glycoprotein, has recently been cloned from peripheral blood T-cells as described in Spriggs et al., *J. Exp. Med.* 176:1543 (1992), and in U.S. patent application Ser. No. 07/969,703, filed Oct. 23, 1992, the disclosure of which is incorporated by reference herein. The cloning of murine CD40L is described in Armitage et al., *Nature* 357:80, 1992. CD40L induces B-cell proliferation in the absence of any co-stimulus, and can also induce production of immunoglobulins in the presence of cytokines.

Monoclonal antibodies to CD40 are known in the art (see, for example, the sections dedicated to B cell antigens in LEUKOCYTE TYPING III; A. J. McMichael ed. Oxford University Press Oxford, and LEUKOCYTE TYPING IV; Oxford University Press. Oxford). Antibodies to CD40 have been demonstrated to exert costimulatory signals on normal B cells, resulting in proliferative and differentiation responses. Similarly, CD40L exerts protein stimulatory or costimulatory signals to normal B cells.

It has been observed that cross-linking of surface IgM on some B cell lymphoma lines exerts inhibitory signals to the lymphoma cells (Beckwith et al., *J. Immunol.* 147:2411, 1991). Similarly, exposure of malignant B or T cells to stimuli that lead to activation of normal lymphocytes can result in growth arrest of the cells (Ashwell et al., *Science* 237:61, 1987; Bridges et al., *J. Immunol.* 139:4242, 1987; Mercep et al., *J. Immunol.* 140:324, 1988; Sussman et al., *J. Immunol.* 140:2520, 1988; Warner and Scott, *Cell. Immunol.* 115:195, 1988; Page and DeFranco, *J. Immunol.* 140:3717, 1988).

Garnier et al. observed that antibodies to CD40 or another B cell marker, CD23, showed some degree of effectiveness at inhibiting lymphoma formation in SCID mice that had been injected with human PBL and then infected with EBV (Abstract 167, XIVth Intl. Congress of the Transplantation Society, 1992). However, it was unknown in the art whether the mechanism of action involved was inhibition of binding of CD40L to CD40 by the anti-CD40 antibody, or by some other means. Therefore, there is a need in the art to determine the effects of other anti-CD40 antibodies, and of CD40L itself, upon B cell lymphomas and other malignant cells that express CD40.

SUMMARY OF THE INVENTION

The present invention relates to a method of treating a mammal afflicted with a disease characterized by neoplastic cells that express CD40, comprising administering a therapeutically effective amount of a CD40 binding protein in a pharmaceutically acceptable buffer. The therapeutically effective amount is from about 0.01 to about 1 mg/kg body weight. CD40 binding proteins may be selected from the group consisting of monoclonal antibodies to CD40, CD40 ligand, and combinations thereof. Particularly preferred monoclonal antibodies are HuCD40-M2 (deposited at the American Type Culture Collection, 12301 Parklawn Dr., Rockville, Md., 20852, USA, under the terms of the Budapest Treaty, and given ATCC accession number HB11459) and HuCD40-M3, which are described in U.S.S.N. 08/526, 014, filed Sep. 8, 1995, now pending, a continuation of U.S.S.N. 08/130, 541, filed Oct. 1, 1993, now abandoned. Oligomeric forms of CD40 ligand are particularly preferred, and include a soluble CD40 ligand-Fc fusion protein, and an oligomeric CD40 leucine zipper fusion protein, both of which have been described in U.S.S.N. 08/477,733, filed Jun. 7, 1995, now pending, and U.S.S.N. 08/484,624, filed Jun. 7, 1995, now pending, both of which are continuations in part of U.S.S.N. 08/249,189, filed May 24, 1994, now pending, which is a continuation in part of U.S.S.N. 07/969, 703, filed Oct. 23, 1992, now abandoned. The present invention also relates to a method of preventing a disease characterized by neoplastic cells that express CD40, in a mammal susceptible to the disease, comprising administering a therapeutically effective amount of a CD40 binding protein in a pharmaceutically acceptable buffer, wherein the therapeutically effective amount is from about 0.01 to about 1 mg/kg body weight. Neoplastic cells that express CD40 include B lymphoma cells, some melanoma cells and some carcinoma cells.

BRIEF DESCRIPTION OF THE DRAWINGS

FIGS. 2A through 2F demonstrate the inhibition of the proliferation of several lymphoma cell lines by antibodies to CD40 (closed squares); in contrast, msIgG did not inhibit proliferation (open squares).

DETAILED DESCRIPTION OF THE INVENTION

Figure 1:
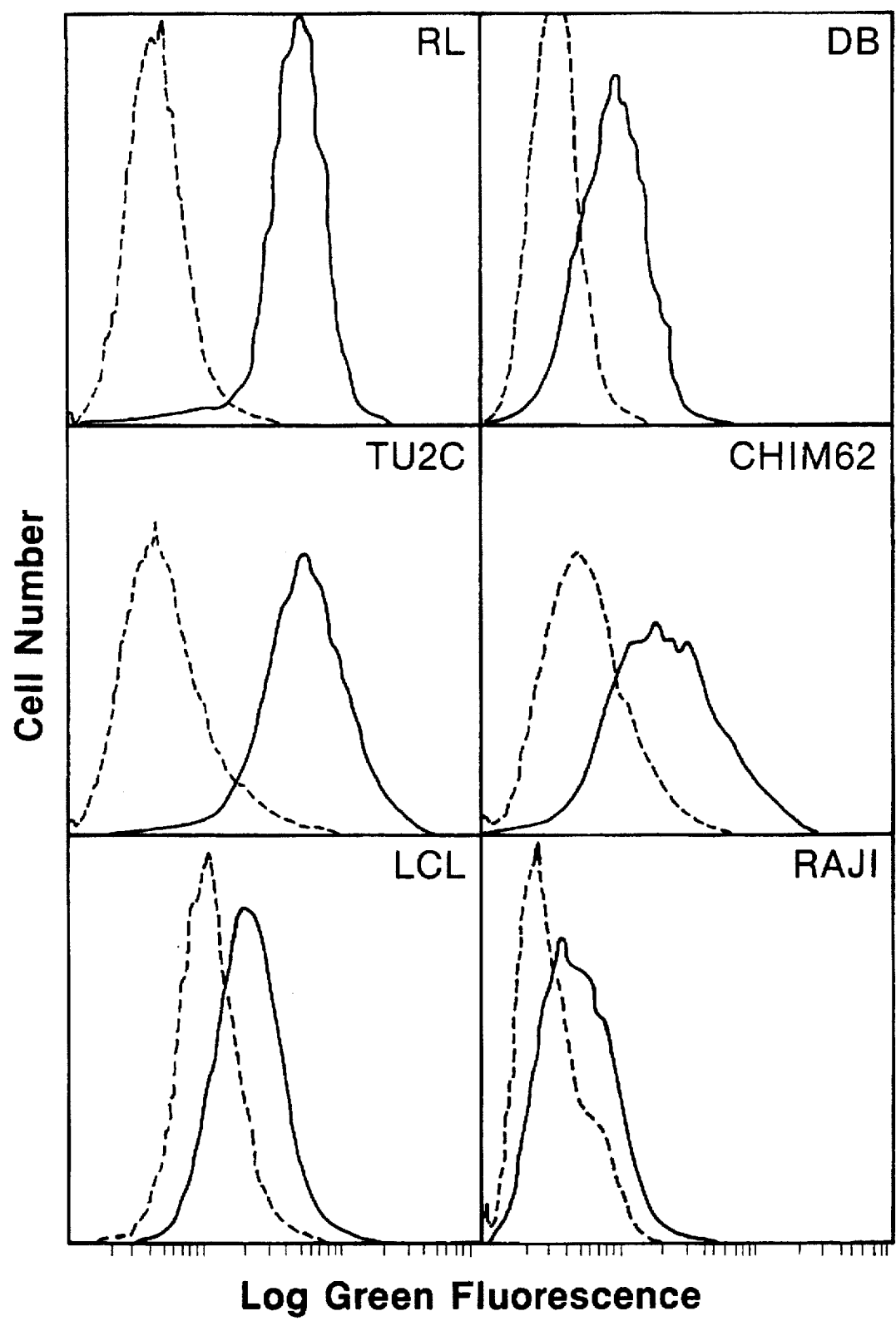
FIG. 1 illustrates the expression of CD40 by several lymphoma cell lines, using anti-CD40 monoclonal antibodies M2 and M3.
Figure 3B:
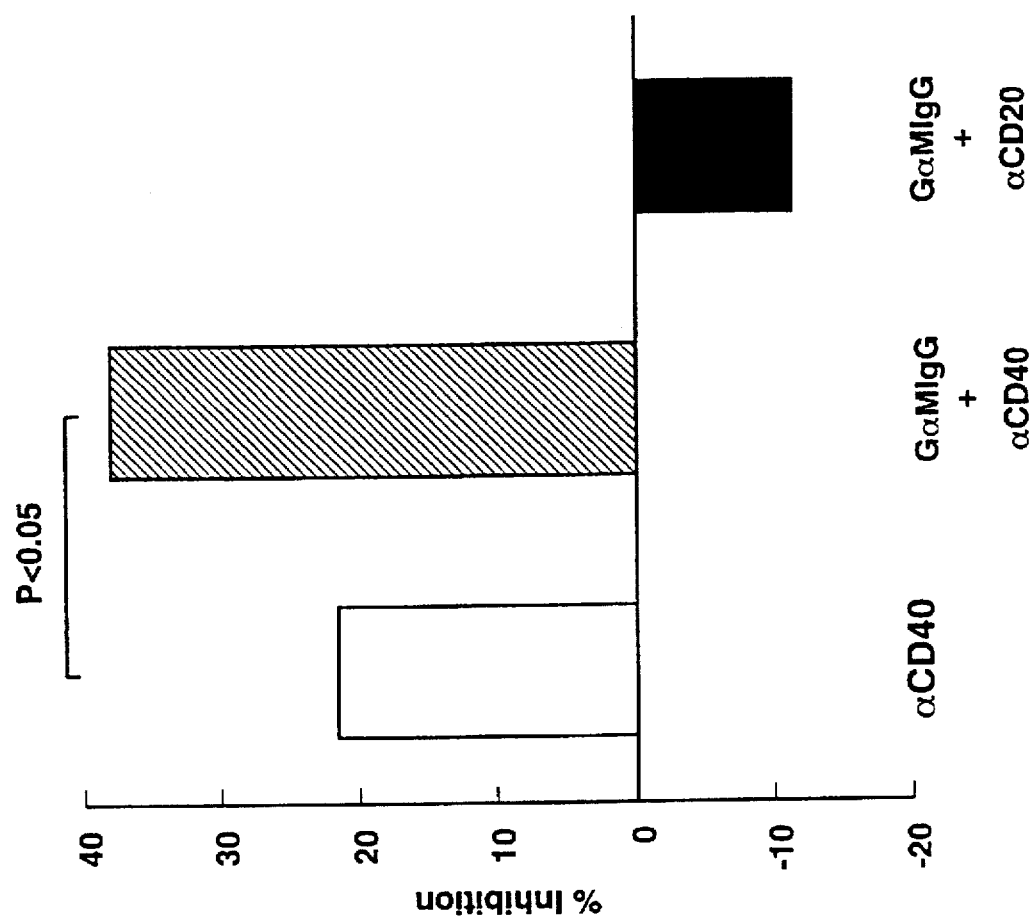
FIG. 3 presents a comparison of the effects of soluble anti-CD40 (panel A) or immobilized anti-CD40 (panel B) on lymphoma growth.
Figure 3A:
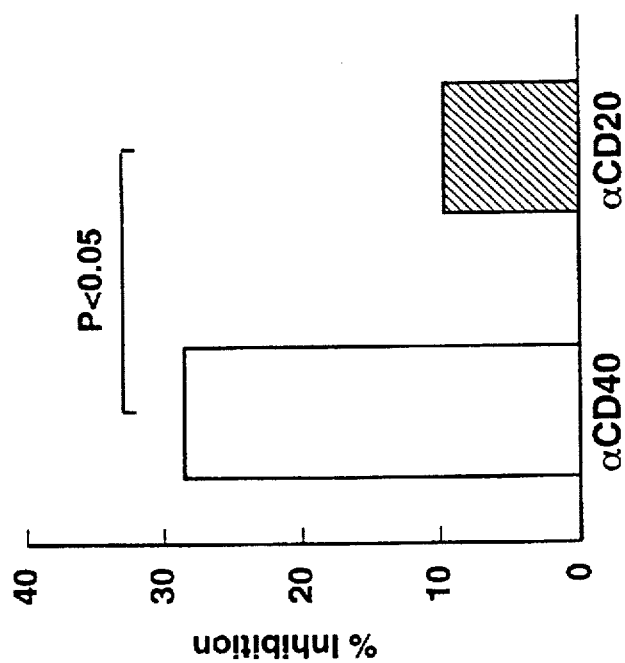

The present invention relates to methods of treating or preventing diseases characterized by neoplastic cells that express a cell surface molecule known as CD40. The inventive methods utilize a protein (or proteins) that specifically bind CD40 (referred to as a CD40 binding protein) in a non-covalent interaction based upon the proper conformation of the CD40 binding protein and CD40 itself. For example, a CD40 binding protein can comprise an extracellular region of a CD40 ligand. In other cases, a CD40 binding protein can comprise an antibody that binds CD40 through an antigen binding region. Additional CD40 binding proteins can be prepared through recombinant methods, by preparation of fusion proteins comprising a CD40 binding region (or domain) from a CD40 ligand, or an antibody to CD40, with a second protein, for example, a human immunoglobulin Fc domain.

CD40

Human CD40 antigen (CD40) is a peptide of 277 amino acids having a molecular weight of 30,600, and a 19 amino acid secretory signal peptide comprising predominantly hydrophobic amino acids (Stamenkovic et al., supra). A cDNA encoding human CD40 was isolated from a cDNA library prepared from Burkitt lymphoma cell line Raji. The putative protein encoded by the CD40 cDNA contains a putative leader sequence, transmembrane domain and a number of other features common to membrane-bound receptor proteins. CD40 has been found to be expressed on B lymphocytes, epithelial cells and some carcinoma cell lines.

CD40 is a member of the tumor necrosis factor (TNF)/nerve growth factor (NGF) receptor family, which is defined by the presence of cysteine-rich motifs in the extracellular region (Smith et al., Science 248:1019, 1990; Mallett and Barclay, Immunology Today 12:220; 1991). This family includes the lymphocyte antigen CD27, CD30 (an antigen found on Hodgkin's lymphoma and Reed-Sternberg cells), two receptors for TNF, a murine protein referred to as 4-1BB, rat OX40 antigen, NGF receptor, and Fas antigen.

CD40 may be detected on the surface of a cell by any one of several means known in the art. For example, an antibody specific for CD40 may be used in a fluorescence-activated cell sorting technique to determine whether cells express CD40, as described in Example 1 herein. Other methods of detecting cell surface molecules are also useful in detecting CD40.

CD40 Monoclonal Antibodies

Monoclonal antibodies directed against the CD40 surface antigen (CD40 mAb) have been shown to mediate various biological activities on human B cells. For example, CD40 mAb induce homotypic and heterotypic adhesions (Barrett et al., J. Immunol. 146:1722, 1991; Gordon et al., J. Immunol. 140:1425, 1988), and increase cell size (Gordon et al., J. Immunol. 140:1425, 1988; Valle et al., Eur. J. Immunol. 19:1463, 1989). CD40 mAb also induce proliferation of B cells activated with anti-IgM, CD20 mAb, or phorbol ester alone (Clark and Ledbetter, Proc. Natl. Acad. Sci. USA 83:4494, 1986; Gordon et al., LEUKOCYTE TYPING III; A. J. McMichael ed. Oxford University Press. Oxford, p. 426; Paulie et al., J. Immunol. 142:590, 1989) or in concert with IL-4 (Valle et al., Eur. J. Immunol. 19:1463, 1989; Gordon et al., Eur. J. Immunol. 17:1535, 1987), and produce IgE (Jabara et al., J. Exp. Med. 172:1861, 1990; Gascan et al., J. Immunol. 147:8, 1991), IgG, and IgM (Gascan et al., J. Immunol. 147:8, 1991) from IL-4-stimulated T cell-depleted cultures.

In addition, CD40 mAb have been reported to enhance IL-4-mediated soluble CD23/FcεRII release from B cells (Gordon and Guy, Immunol. Today 8:339, 1987; Cairns et al., Eur. J. Immunol. 18:349, 1988) and to promote B cell production of IL-6 (Clark and Shu, J. Immunol. 145:1400, 1990). Recently, in the presence of $CD_w32+$ adherent cells, human B cell lines have been generated from primary B cell populations with IL-4 and CD40 mAb (Banchereau et al., Science 241:70, 1991). Furthermore, germinal center centrocytes can be prevented from undergoing apoptosis if they are activated through CD40 and/or receptors for antigen (Liu et al., Nature 342:929, 1989). Each of the above publications describes CD40 mAb that stimulate a biological activity of B cells.

U.S.S.N. 08/526,014, filed Sep. 8, 1995, now pending, a continuation of U.S.S.N. 08/130, 541, filed Oct. 1, 1993, now abandoned, the relevant disclosure of which is incorporated by reference, discloses two monoclonal antibodies to CD40, referred to as HuCD40-M2 and HuCD40-M3. Unlike other CD40 mAb, HuCD40-M2 (ATCC HB11459) and HuCD40-M3 bind CD40 and inhibit binding of CD40 to cells that constitutively express CD40L. Greater than 90% inhibition of binding was observed with HuCD40-M2 or with CD40 mAb M3, at concentrations as low as 12.5 µg/ml, as compared to irrelevant IgG or a control CD40 mAb, G28.5. HuCD40-M2 was also able to inhibit CD40L-induced TNF-α production.

CD40 mAb HuCD40-M2 (M2) and HuCD40-M3 (M3) were shown to inhibit binding of huCD40.Fc to huCD40L as follows. Purified human peripheral blood T cells were stimulated for 18 hrs with PMA and ionomycin to induce human CD40L expression. The T cells were then bound with human IL-4R.Fc (5 µg/ml) as a negative control protein or with huCD40.Fc (5 µg/ml) and binding inhibition performed with irrelevant ms IgG (20 µg/ml), with CD40 mAb M2 (20 µg/ml) or with CD40 mAb M3 (20 µg/ml). The bound CD40.Fc was detected by flow cytometric analysis with an anti human Fc Ab-biotin and streptavidin-phycoerythrin. At these concentrations both CD40 M2 and M3 inhibited CD40.Fc binding by >90% as compared to irrelevant ms IgG.

CD40 mAb M2 and M3 were shown to inhibit binding of huCD40.Fc to muCD40 as follows. EL40.9 cells that constitutively express muCD40L were bound with control protein or with a sub-optimal concentration of huCD40.Fc biotin (2.5 µg/ml) and binding inhibition performed with irrelevant ms IgG (50 µg/ml), a control ms IgG1 mAb G28.5 (50 µg/ml) (provided by Dr. Edward A. Clark, University of Washington), with CD40 mAb M2 (12.5 µg/ml) or with CD40 mAb M3 (12.5 µg/ml) . The bound biotin-labeled CD40.Fc was detected by flow cytometric analysis using streptavidin-phycoerythrin. At these concentrations both CD40 mAb M2 and M3 inhibited CD40.Fc binding by >95% as compared to irrelevant ms IgG or ms IgG1 mAb G28.5.

Additional CD40 monoclonal antibodies may be generated using conventional techniques (see U.S. Pat. Nos. RE 32,011, 4,902,614, 4,543,439, and 4,411,993 which are incorporated herein by reference; see also *Monoclonal Antibodies, Hybridomas: A New Dimension in Biological Analyses*, Plenum Press, Kennett, McKearn, and Bechtol (eds.), 1980, and *Antibodies: A Laboratory Manual*, Harlow and Lane (eds.), Cold Spring Harbor Laboratory Press, 1988, which are also incorporated herein by reference).

Briefly, an animal is injected with a form of CD40 suitable for generating an immune response against CD40. The animal may be reimmunized as needed until levels of serum antibody to CD40 have reached a plateau, then be given a final boost of soluble CD40, and three to four days later sacrificed. Organs which contain large numbers of B cells such as the spleen and lymph nodes are harvested and disrupted into a single cell suspension by passing the organs through a mesh screen or by rupturing the spleen or lymph node membranes which encapsulate the cells.

Alternatively, suitable cells for preparing monoclonal antibodies are obtained through the use of in vitro immunization techniques. Briefly, an animal is sacrificed and the spleen and lymph node cells are removed. A single cell suspension is prepared, and the cells are placed into a culture which contains a form of CD40, which is suitable for generating an immune response as described above. Subsequently, the lymphocytes are harvested and fused as described below.

Cells which are obtained through the use of in vitro immunization or from an immunized animal as described above may be immortalized by transfection with a virus such as the Epstein bar virus (EBV) (see Glasky and Reading, *Hybridoma* 8(4):377–389, 1989). Alternatively, the harvested spleen and/or lymph node cell suspensions are fused with a suitable myeloma cell in order to create a "hybridoma" which secretes monoclonal antibody. Suitable myeloma lines are preferably defective in the construction or expression of antibodies, and are additionally syngeneic with the cells from the immunized animal. Many such myeloma cell lines are well known in the art and may be obtained from sources such as the American Type Culture Collection (ATCC), Rockville, Md. (see *Catalogue of Cell Lines & Hybridomas*, 6th ed., ATCC, 1988).

CD40 Ligand

Activated CD4+ T cells express high levels of a ligand for CD40 (CD40L). Human CD40L, a membrane-bound glycoprotein, has recently been cloned from peripheral blood T-cells as described in Spriggs et al., *J. Exp. Med.* 176:1543 (1992), and in U.S.S.N. 08/477,733, filed Jun. 7, 1995, now pending, and U.S.S.N. 08/484,624, filed Jun. 7, 1995, now pending, both of which are continuations in part of U.S.S.N. 08/249,189, filed May 24, 1994, now pending, which is a continuation in part of U.S. patent application Ser. No. 07/969,703, filed Oct. 23, 1992, now abandoned, the disclosure of which is incorporated by reference herein. The cloning of murine CD40L is described in Armitage et al., *Nature* 357:80, 1992. CD40L induces B-cell proliferation in the absence of any co-stimulus, and can also induce production of immunoglobulins in the presence of cytokines.

CD40L is a type II membrane polypeptide having an extracellular region at its C-terminus, a transmembrane region and an intracellular region at its N-terminus. Soluble CD40L comprises an extracellular region of CD40L (amino acid 47 to amino acid 261 of SEQ ID NO:1) or a fragment thereof. CD40L biological activity is mediated by binding of the extracellular region of CD40L with CD40, and includes B cell proliferation and induction of antibody secretion (including IgE secretion).

U.S.S.N. 07/969,703 describes preparation of a soluble CD40L/Fc fusion protein referred to as CD40L/FC2. CD40L/FC2 contains an eight amino acid hydrophilic sequence described by Hopp et al. (Hopp et al., *Bio/Technology* 6:1204,1988; referred to as Flag®), an IgG$_1$ Fc domain, a [Gly$_4$Ser]$_3$ linker sequence (described in U.S. Pat. No. 5,073,627), and the extracellular region of human CD40L. Also described in U.S.S.N. 07/969,703 is a soluble CD40L fusion protein referred to as trimeric CD40L, which contains a 33 amino acid sequence referred to as a "leucine zipper," the eight amino acid hydrophilic sequence described by Hopp et al. (*supra*), followed by the extracellular region of human CD40L. Both oligomeric forms of CD40L induce human B cell proliferation in the absence of any co-stimuli, and (in conjunction with the appropriate cytokine) result in the production of IgG, IgE, IgA and IgM.

The CD40L/FC2 and the trimeric CD40L described in U.S.S.N. 07/969,703 will be useful in the present inventive methods, as will other forms of CD40L that can be prepared using known methods of preparing recombinant proteins. Such recombinant proteins include novel polypeptides that can act as a ligand for murine and human CD40, which have been isolated and sequenced. More particularly, cDNAs encoding these ligands have been cloned and sequenced as described in USSN 07/969,703, filed Oct. 23, 1992. Further provided therein are methods for expression of recombinant CD40L polypeptides. CD40L polypeptide include other forms of mammalian CD40L, such as derivatives or analogs of human or murine CD40L. Murine and human CD40L comprise a 214 and 215, respectively amino acid extracellular region at the C-terminus of full length, membrane-bound polypeptide. The extracellular region contains the domain that binds to CD40. Murine and human CD40L further comprise a homologous hydrophobic 24 amino acid transmembrane region delineated by charged amino acids on either side and a 22 amino acid intracellular region at their N-termini. The present invention further comprises full length CD40L polypeptides or fragments thereof comprising all or part of the extracellular region or derivatives of the extracellular region and mammalian cells transfected with a cDNA encoding murine or human CD40L and expressing human or murine CD40 L as a membrane-bound protein.

The present invention comprises isolated DNA sequences encoding CD40L polypeptides and DNA or RNA sequences complementary to such isolated DNA sequences. The isolated DNA sequences and their complements are selected from the group consisting of (a) nucleotides 184 through 828, 193 through 828, 193 through 762, or 403 through 762 of the DNA sequence set forth in SEQ ID NO:1 and their complements, (b) DNA sequences which hybridize to the DNA sequences of (a) or their complements under conditions of moderate stringency and which encode a CD40L polypeptide, analogs or derivatives thereof, and (c) DNA sequences which, due to the degeneracy of the genetic code, encode CD40L polypeptides encoded by any of the foregoing DNA sequences and their complements. In addition, the present invention includes vectors comprising DNA sequences encoding CD40L polypeptides and analogs, and host cells transfected with such vectors The novel cytokine disclosed herein is a ligand for CD40, a receptor that is a member of the TNF receptor super family. Therefore, CD40L is likely to be responsible for transducing signal via CD40, which is known to be expressed, for example, by B lymphocytes. Full-length CD40L is a membrane-bound polypeptide with an extracellular region at its C terminus, a transmembrane region, and an intracellular region at its N-terminus. A soluble version of CD40L can be made from the extracellular region or a fragment thereof and a soluble CD40L has been found in culture supernatants from cells that express a membrane-bound version of CD40L. The protein sequence of the extracellular region of murine CD40L extends from amino acid 47 to amino acid 260 in SEQ ID NO:2 of USSN 07/969,703. The protein sequence of the extracellular region of human CD40L extends from amino acid 47 to amino acid 261 in SEQ ID NO:2. The biological activity of CD40L is mediated by binding to CD40or a species-specific homolog thereof and comprises proliferation of B cells and induction of immunoglobulin secretion from activated B cells. CD40L (including soluble monomeric and oligomeric forms, as well as membrane-bound forms) can effect B cell proliferation and immunoglobulin secretion (except IgE secretion) without the presence of added IL-4, in contrast to anti-CD40 antibodies, which require IL-4 and cross-linking to mediate activity.

CD40L refers to a genus of polypeptides which are capable of binding CD40, or mammalian homologs of CD40. As used herein, the term "CD40L" includes soluble CD40L polypeptides lacking transmembrane and intracellular regions, mammalian homologs of human CD40L, analogs of human or murine CD40L or derivatives of human or murine CD40L.

CD40L may also be obtained by mutations of nucleotide sequences coding for a CD40L polypeptide. A CD40L analog, as referred to herein, is a polypeptide substantially homologous to a sequence of human or murine CD40L but which has an amino acid sequence different from native sequence CD40L (human or murine species) polypeptide because of one or a plurality of deletions, insertions or substitutions. Analogs of CD40L can be synthesized from DNA constructs prepared by oligonucleotide synthesis and ligation or by site-specific mutagenesis techniques.

The primary amino acid structure of human or murine CD40L may be modified to create CD40L derivatives by forming covalent or aggregative conjugates with other chemical moieties, such as glycosyl groups, lipids, phosphate, acetyl groups and the like, or by creating amino acid sequence mutants. Covalent derivatives of CD40L are prepared by linking particular functional groups to CD40L amino acid side chains or at the N-terminus or C-terminus of a CD40L polypeptide or the extracellular domain thereof. Other derivatives of CD40L within the scope of this invention include covalent or aggregative conjugates of CD40L or its fragments with other proteins or polypeptides, such as by synthesis in recombinant culture as N-terminal or C-terminal fusions. For example, the conjugate may comprise a signal or leader polypeptide sequence at the N-terminal region or C-terminal region of a CD40L polypeptide which co-translationally or post-translationally directs transfer of the conjugate from its site of synthesis to a site inside or outside of the cell membrane or cell wall (e.g. the α-factor leader of *Saccharomyces*). CD40L polypeptide fusions can comprise polypeptides added to facilitate purification and identification of CD40L (e.g. poly-His), or fusions with other cytokines to provide novel polyfunctional entities.

Nucleic acid sequences within the scope of the present invention include DNA and/or RNA sequences that hybridize to the nucleotide sequence of SEQ ID NO:1 or the complementary strand, under conditions of moderate or severe stringency. Moderate stringency hybridization conditions refer to conditions described in, for example, Sambrook et al. *Molecular Cloning: A Laboratory Manual*, 2 ed. Vol. 1, pp. 1.101–104, Cold Spring Harbor Laboratory Press, (1989). Conditions of moderate stringency, as defined by Sambrook et al., include use of a prewashing solution of 5 X SSC, 0.5% SDS, 1.0 mM EDTA (pH 8.0) and hybridization conditions of 50° C., 5 X SSC, overnight. Conditions of severe stringency include higher temperatures of hybridization and washing. (for example, hybridization in 6 X SSC at 63° C. overnight; washing in 3 X SSC at 55° C.).

Soluble forms of some transmembrane proteins have been expressed as fusion proteins in which an extracellular domain of a membrane protein (cognate binding region) is joined to an immunoglobulin heavy chain constant (Fc) domain. Such fusion proteins are useful as reagents to detect their cognate proteins. They are also useful as therapeutic agents in treatment of disease. However, receptors for Fc domains are present on many cell types. Thus, when a fusion protein is formed from an Fc domain and a cognate binding region, binding to a cell may occur either through binding of the cognate binding region to its cognate protein, or through binding of the Fc domain to an Fc receptor (FcR). Such binding of the Fc domain to Fc receptors may overwhelm any binding of the cognate binding region to its cognate. Moreover, binding of Fc domains to Fc receptors induces secretion of various cytokines that are involved in upregulating various aspects of an immune or inflammatory response; such upregulation has been implicated in some of the adverse effects of therapeutic administration of certain antibodies (Krutman et al., *J. Immunol.* 145:1337, 1990; Thistlewaite et al., *Am. J. Kidney Dis.* 11:112, 1988).

Jefferis et al. (*Mol. Immunol.* 27:1237; 1990) reported that a region of an antibody referred to as the hinge region (and specifically residues 234–237 within this region) determine recognition of the antibody by human Fc receptors FcγRI, FcγRII, and FcγRIII. Leu$_{(234)}$ and Leu$_{(235)}$ were critical to high affinity binding of IgG$_3$ to FcγRI present on U937 cells (Canfield and Morrison, *J. Exp. Med.* 173:1483; 1991). Similar results were obtained by Lurid et al. (*J. Immunol.* 147:2657, 1991; *Molecular Immunol.* 29:53, 1991). These authors observed 10–100 fold decrease in affinity of IgG for FcR when a single amino acid substitution was made at a critical residue.

A single amino acid substitution in the Fc domain of an anti-CD3 monoclonal antibody (leucine to glutamic acid at position 235) was found to result in significantly less T cell activation than unmutagenized antibody, while maintaining the immunosuppressive properties (Alegre et al., *J. Immunol.* 148:3461; 1992). Wawrzynczak et al. found that murine monoclonal antibodies that contained a single amino acid substitution at residue 235 had the same serum half-life as did native antibodies (*Mol. Immunol.* 29:221; 1992). Fc domains with reduced affinity for Fc receptors are useful in the preparation of Fc fusion proteins.

Leucine zippers were originally identified in several DNA-binding proteins (Landschulz et al., *Science* 240:1759, 1988). Leucine zipper domain is a term used to refer to a conserved peptide domain present in these (and other) proteins, which is responsible for dimerization of the proteins. The leucine zipper domain (also referred to herein as an oligomerizing, or oligomer-forming, domain) comprises a repetitive heptad repeat, with four or five leucine residues interspersed with other amino acids. Examples of leucine zipper domains are those found in the yeast transcription factor GCN4 and a heat-stable DNA-binding protein found in rat liver (C/EBP; Landschulz et al., *Science* 243:1681, 1989). Two nuclear transforming proteins, fos and jun, also exhibit leucine zipper domains, as does the gene product of the murine proto-oncogene, c-myc (Landschulz et al., *Sci-*

*ence* 240:1759, 1988). The products of the nuclear oncogenes fos and jun comprise leucine zipper domains preferentially form a heterodimer (O'Shea et al., *Science* 245:646, 1989; Turner and Tjian, *Science* 243:1689, 1989). The leucine zipper domain is necessary for biological activity (DNA binding) in these proteins.

The fusogenic proteins of several different viruses, including paramyxovirus, coronavirus, measles virus and many retroviruses, also possess leucine zipper domains (Buckland and Wild, *Nature* 338:547,1989; Britton, *Nature* 353:394, 1991; Delwart and Mosialos, *AIDS Research and Human Retroviruses* 6:703, 1990). The leucine zipper domains in these fusogenic viral promins are near the transmembrane region of the proteins; it has been suggested that the leucine zipper domains could contribute to the oligomeric structure of the fusogenic proteins. Oligomerization of fusogenic viral proteins is involved in fusion pore formation (Spruce et al, *Proc. Natl. Acad. Sci. U.S.A.* 88:3523, 1991).

Leucine zipper domains have also been recently reported to play a role in oligomerization of heat-shock transcription factors (Rabindran et al., *Science* 259:230, 1993).

Leucine zipper domains fold as short, parallel coiled coils. (O'Shea et al., *Science* 254:539; 1991) The general architecture of the parallel coiled coil has been well characterized, with a "knobs-into-holes" packing as proposed by Crick in 1953 (*Acta Crystallogr.* 6:689). The dimer formed by a leucine zipper domain is stabilized by the heptad repeat, designated (abcdefg)$_n$ according to the notation of McLachlan and Stewart (*J. Mol. Biol.* 98:293; 1975), in which residues a and d are generally hydrophobic residues, with d being a leucine, which line up on the same face of a helix. Oppositely-charged residues commonly occur at positions g and e. Thus, in a parallel coiled coil formed from two helical leucine zipper domains, the "knobs" formed by the hydrophobic side chains of the first helix are packed into the "holes" formed between the side chains of the second helix.

The leucine residues at position d contribute large hydrophobic stabilization energies, and are important for dimer formation (Krystek et al., *Int. J. Peptide Res.* 38:229, 1991). Lovejoy et al. recently reported the synthesis of a triple-stranded α-helical bundle in which the helices run up-up-down (*Science* 259:1288, 1993). Their studies confirmed that hydrophobic stabilization energy provides the main driving force for the formation of coiled coils from helical monomers. These studies also indicate that electrostatic interactions contribute to the stoichiometry and geometry of coiled coils.

Several studies have indicated that conservative amino acids may be substituted for individual leucine residues with minimal decrease in the ability to dimerize; multiple changes, however, usually result in loss of this ability (Landschulz et al., *Science* 243:1681, 1989; Turner and Tjian, *Science* 243:1689, 1989; Hu et al., *Science* 250:1400, 1990). van Heekeren et al. reported that a number of different amino residues can be substituted for the leucine residues in the leucine zipper domain of GCN4, and further found that some GCN4 proteins containing two leucine substitutions were weakly active (*Nucl. Acids Res.* 20:3721, 1992). Mutation of the first and second heptadic leucines of the leucine zipper domain of the measles virus fusion protein (MVF) did not affect syncytium formation (a measure of vitally-induced cell fusion); however, mutation of all four leucine residues prevented fusion completely (Buckland et al., *J. Gen. Virol.* 73:1703, 1992). None of the mutations affected the ability of MVF to form a tetramer.

Recently, amino acid substitutions in the a and d residues of a synthetic peptide representing the GCN4 leucine zipper domain have been found to change the oligomerization properties of the leucine zipper domain (Alber, Sixth Symposium of the Protein Society, San Diego, Calif.). When all residues at position a are changed to isoleucine, the leucine zipper still forms a parallel dimer. When, in addition to this change, all leucine residues at position d are also changed to isoleucine, the resultant peptide spontaneously forms a trimeric parallel coiled coil in solution. Substituting all amino acids at position d with isoleucine and at position a with leucine results in a peptide that tetramerizes. Peptides containing these substitutions are still referred to as leucine zipper domains since the mechanism of oligomer formation is believed to be the same as that for traditional leucine zipper domains such as those described above.

Additional CD40 Binding Proteins

Binding proteins may also be constructed utilizing recombinant DNA techniques to incorporate the variable regions of a gene which encodes an antibody to CD40. (see James W. Larrick et al., "Polymerase Chain Reaction Using Mixed Primers: Cloning of Human Monoclonal Antibody Variable Region Genes From Single Hybridoma Cells," *Biotechnology* 7:934–938, Sep. 1989; Reichmann et al., "Reshaping Human Antibodies for Therapy," *Nature* 332:323–327, 1988; Roberts et al., "Generation of an Antibody with Enhanced Affinity and Specificity for its Antigen by Protein Engineering," *Nature* 328:731–734, 1987; Verhoeyen et al., "Reshaping Human Antibodies: Grafting an Antilysozyme Activity," *Science* 239:1534–1536, 1988; Chaudhary et al., "A Recombinant Immunotoxin Consisting of Two Antibody Variable Domains Fused to Pseudomonas Exotoxin," *Nature* 339:394–397, 1989).

Briefly, DNA encoding the antigen-binding site (or CD40binding domain; variable region) of a CD40 mAb is isolated, amplified, and linked to DNA encoding another protein, for example a human IgG (see Verhoeyen et al., *supra;* see also Reichmann et al., *supra*). Alternatively, the antigen-binding site (variable region) may be either linked to, or inserted into, another completely different protein (see Chaudhary et al., *supra*), resulting in a new protein with antigen-binding sites of the antibody as well as the functional activity of the completely different protein.

Furthermore, DNA sequences which encode smaller portions of the antibody or variable regions which specifically bind to mammalian CD40 may also be utilized within the context of the present invention. Similarly, the CD40 binding region (extracellular domain) of a CD40 ligand may be used to prepare other CD40 binding proteins. DNA sequences that encode proteins or peptides that form oligomers will be particularly useful in preparation of CD40 binding proteins comprising an antigen binding domain of CD40 antibody, or an extracellular domain of a CD40 ligand. Certain of such oligomer-forming proteins are disclosed in U.S.S.N. 08/477,733, and U.S.S.N. 08/484,624, both of which are continuations in part of U.S.S.N. 08/249,189, which is a continuation in part of U.S.S.N. 07/969,703, now abandoned; additional, useful oligomer-forming proteins are also disclosed in U.S.S.N. 08/446,922, filed May 18, 1995, now pending, a continuation in part of U.S.S.N. 08/107,353, filed Aug. 13, 1993, now abandoned.

Once suitable antibodies or binding proteins have been obtained, they may be isolated or purified by many techniques well known to those of ordinary skill in the art (see *Antibodies: A Laboratory Manual,* Harlow and Lane (eds.), Cold Spring Harbor Laboratory Press, 1988). Suitable techniques include peptide or protein affinity columns, HPLC or RP-HPLC, purification on protein A or protein G columns, or any combination of these techniques. Recombinant CD40 binding proteins can be prepared according to standard methods, and tested for binding specificity to the CD40 utilizing assays known in the art, including for example ELISA, ABC, or dot blot assays, as well by bioactivity assays such as those described for CD40 mAb.

SCID mouse models

The term SCID (severe combined immune deficiency) mouse refers to a mutant C.B-17 strain of mouse with a chromosome 16 deficiency that prevents correct T cell receptor and immunoglobulin gene rearrangement, and is thus virtually devoid of functional B and T cells (Bosma et al., *Nature* 301:257; 1983). SCID mice can be successfully reconstituted with human fetal lymphoid tissues, and with adult human lymphocytes, and have thus been useful as a model for studying human immune function in vivo (Mosier et at., *Nature* 335:256, 1988; McKune et al., *Science* 241:1632, 1988; Kamel-Reid and Dick, *Science* 242:1707, 1988). SCID mice reconstituted with human peripheral blood lymphocytes (PBL) from individuals with serological evidence of Epstein-Barr virus (EBV) infection often develop lymphomas of B cell origin (Mosier et al. *supra*; Cannon et al., *J. Clin. Invest.* 85:1333, 1990; Rowe et al., *J. Exp. Med.* 173:147, 1991; Purtilo et al., *Int. J. Cancer* 47:510, 1991). Veronese et al. reported that the presence of functional T cells in the injected PBL was absolutely necessary for progression of latently EBV-infected B cells into tumor masses (*J. Exp. Med.* 176:1763, 1992). The lymphomas that develop in this SCID mouse model are highly aggressive, and analogous to EBV-lymphomas that arise in immunocompromised individuals.

Administration of CD40 Binding Protein Compositions

The present invention provides therapeutic compositions comprising an effective amount of a CD40 binding protein in a suitable diluent or carrier and methods of treating mammals using the compositions. For therapeutic use, purified CD40 binding protein or a biologically active analog thereof is administered to a patient, preferably a human, for treatment in a manner appropriate to the indication. Thus, for example, CD40 binding protein pharmaceutical compositions (for example, in the form of a soluble extracellular domain of CD40 ligand, or a fragment thereof, or a monoclonal antibody to CD40) which is administered to achieve a desired therapeutic effect can be given by bolus injection, continuous infusion, sustained release from implants, or other suitable technique.

Typically, a CD40 binding protein therapeutic agent will be administered in the form of a pharmaceutical composition comprising purified CD40 binding protein in conjunction with physiologically acceptable carriers, excipients or diluents. Such carriers will be nontoxic to patients at the dosages and concentrations employed. Ordinarily, the preparation of such compositions entails combining a CD40 binding protein with buffers, antioxidants such as ascorbic acid, low molecular weight (less than about 10 residues) polypeptides, proteins, amino acids, carbohydrates including glucose, sucrose or dextrans, chelating agents such as EDTA, glutathione and other stabilizers and excipients. Neutral buffered saline or saline mixed with conspecific serum albumin are exemplary appropriate diluents.

Appropriate dosages may be determined by methods that are known in the art. Typically, therapeutically effective dosages of CD40 binding proteins will be in the range of from about 0.01 to about 1 mg/kg body weight. Moreover, CD40 binding proteins may also be used in conjugates of, or combination with, drugs, toxins or radioactive compounds. Preparation of such conjugates for treatment of various diseases are known in the art (see, for example, Waldmann, *Science* 252:1657, 1991).

Prevention or treatment

These results presented herein indicate that CD40 binding proteins may be of significant clinical use not only in the treatment of B-cell lymphomas, but also in the prevention of EBV-induced B-cell lymphoma that can occur after transplantation or in other instances of immunosuppression, such as AIDS, and which present a significant risk in such patient populations. Since CD40 binding proteins can inhibit various B-cell lymphomas directly, it may not be necessary to use them in conjugates of toxins or radioactive compounds, thereby avoiding toxicity and potential negative effects on normal B cells.

The inventive methods may be useful in prevention of immunoblastic B-cell lymphomas that frequently arise in immunocompromised individuals. In such preventative methods, a mammal at risk of developing an immunoblastic B-cell lymphoma is administered CD40 binding protein. The CD40 binding proteins can be administered for as long as the state of immunocompromise that places the individual at risk exists.

Similarly, the results indicate that the inventive methods may be used to prevent occurrence (or reoccurrence) of neoplastic disease characterized by other types of malignant cells that express CD40 in individuals at risk for such disease. Individuals that are considered at risk in these instances include those with family history or other genetic characteristics indicating predisposition to cancers in which the neoplastic cells express CD40, and individuals that develop drag-resistant neoplastic disease as a result of chemotherapy, in which the drug-resistant neoplastic cells express CD40.

Individuals afflicted with disease characterized by neoplastic cells that express CD40 may also be treated according to the inventive methods. The term treatment, as it is generally understood in the art, refers to initiation of therapy after clinical symptoms or signs of disease have been observed. The inventive methods may be used in conjunction with other therapies appropriate for afflicted individuals, including chemotherapy, radiation therapy, and immunotherapy.

The relevant disclosures of all references cited herein are specifically incorporated by reference. The following examples are intended to illustrate particular embodiments, and not limit the scope, of the invention.

EXAMPLE 1

This example describes the characterization of human B-cell lymphoma cells and cell lines. Cells used included RL and DB, cell lines obtained from patients with diffuse, large cell lymphomas of B-cell origin (Beckwith et al., supra), and TU2C and CHIM62, EBV-induced lymphomas obtained from SCID mice that had been injected with PBL from EBV-seropositive individuals. These cells were maintained in culture under standard culture conditions for less than six months prior to initiation of the study. Other cells included Raji, a cell line cultured from a patient with Burkitt's lymphoma, and LCL-2311, a lymphoblastoid cell line generated by infecting human PBL with EBV in vitro.

All of the cell lines were positive for CD40 expression by flow cytometry, using anti-CD40 monoclonal antibodies M2 and M3; results are shown in FIG. 1. RL, DB, and Raji cells were homogeneous in their expression of CD40, whereas the EBV-induced lymphomas from SCID mice were heterogeneous in the staining intensity with anti-CD40. Lymphomas from these mice have previously been demonstrated to be heterogeneous and oligoclonal (Nakamine et al., *Am J. Pathol.* 142:139, 1993), which may account for the differential expression of CD40. CD20, another B cell marker, was also present on the tumor cells.

EXAMPLE 2

This example describes the effect of anti-CD40 antibodies (M2 and M3) on the proliferative potential of lymphoma cells and cell lines in vitro. Proliferation was determined using an assay substantially as described by Rowe et al. (*J. Exp. Med.* 173:147, 1991). Briefly, cell lines were split 24 hours before assays were performed. Cells were resuspended in culture medium to a concentration of $1 \times 10^5$/ml, and 100 µl of cell suspension was plated in 96-well, round bottom microtiter plates (Corning Glass Works, Corning N.Y., USA) already containing 100 µl of appropriately diluted reagents (monoclonal anti-CD40 antibodies M2 and M3, obtained from Immunex Corporation, Seattle, Wash., USA, or mouse IgG myeloma protein (msIgG) purchased from Cappel, Westchester, Pa., USA). Seventy-two hours later, 1 µCi of [$^3$H]-thymidine/well (specific activity 6.7 Ci/mmol; New England Nuclear Research Products, Boston, Mass., USA) was added for the final 8 to 18 hours of culture. Cultures were harvested onto glass fiber filters with a PhDCell Harvesting System (Cambridge Technology Inc., Cambridge, Mass. USA), and [$^3$H]-thymidine uptake was assayed by liquid scintillation using an LKB B-counter (LKB Instruments Inc., Turku, Finland). Each experiment was performed four to six times, with the results of a representative experiment being presented in FIGS. 2A through 2F.

Incubation with anti-CD40 monoclonal antibodies M2 and M3 resulted in significant inhibition of the proliferation of RL, DB, LCL-2311 and EBV-lymphoma cell lines tested, with an optimal inhibition of 40–60% occurring at 1–10 µg/ml of soluble antibody, depending on the lymphoma cell. The Raji cell line did not appear to be significantly affected by soluble anti-CD40.

The effects of soluble anti-CD40 on lymphoma growth were then compared to those of immobilized anti-CD40. Briefly, wells were incubated overnight at 37° C. with goat anti-mouse antibody. Monoclonal anti-CD40 antibodies M2, M3, an anti-CD20 monoclonal antibody provided by Dr. Kevin Conlon (Laboratory of Experimental Immunology, BRMP, NCI-FCRDC, Frederick, Md., USA), or msIgG, at a concentration of 10 µg/ml, were then added to he wells, and the wells were incubated for an additional 4 hours at 37° C. The proliferation assays were then performed as described above; results are shown in 3A and 3B. Immobilization resulted in significantly greater inhibition of proliferation (p<0.05) by the immobilized anti-CD40 antibodies as compared to soluble anti-CD40, or soluble or immobilized anti-CD20. Thus, in contrast to it's effects on normal B cells, stimulation of CD40 exerts inhibitory effects on EBV-induced B lymphomas.

EXAMPLE 3

This example illustrates the effect of CD40 ligand on the growth of B-cell lymphomas in vitro. Soluble CD40 ligand (CD40L; described in U.S.S.N. 08/477,733, and U.S.S.N. 08/484,624, both of which are continuations in part of U.S.S.N. 08/249,189, which is a continuation in part of U.S.S.N. 07/969,703, now abandoned) was obtained from transfected COS-7 cells as supernatant fluid, and tested in a proliferation assay used as described above, in Example 2, using RL or TU2C cells. Both murine and human CD40L-containing supernatant fluids were tested, since murine CD40L binds to human cells that express CD40, and acts as a costimulus in the same manner as human CD40L. Each lot of supernatant fluid was titrated to determine the concentration that yielded optimal inhibition of proliferation; a 1:5 dilution yielded maximal inhibition.

Figure 4:
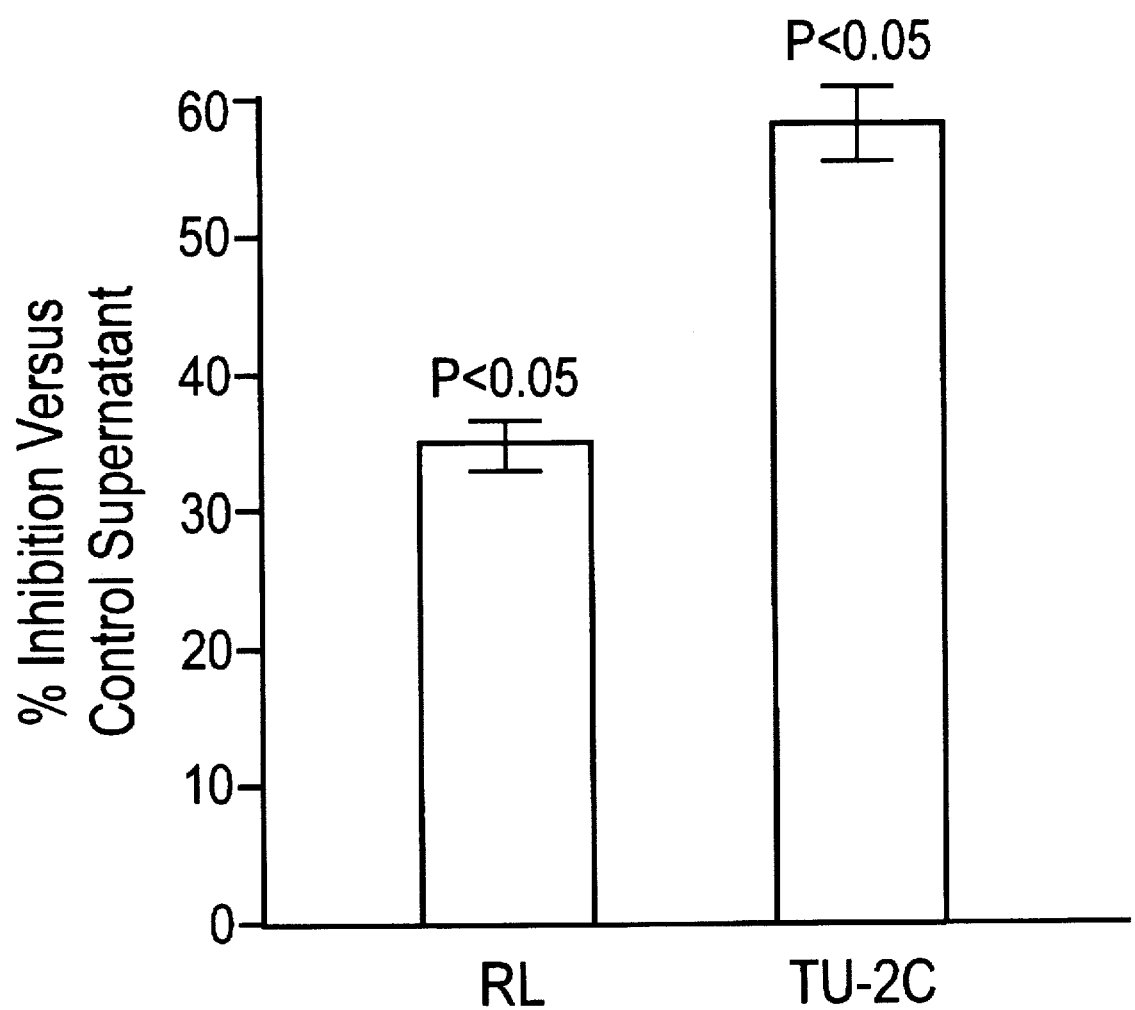
FIG. 4 demonstrates the ability of soluble CD40 ligand to inhibit the growth of B-cell lymphomas in vitro.

Exemplary results are presented in FIG. 4; values are presented as percent of inhibition compared to control supernatant fluids. The soluble human ligand was inhibitory for the various lymphomas tested, with maximal inhibition seen (50–80%) on RL and TU2C cell lines at a 1:5 dilution of the supernatant fluid. The soluble murine CD40L produced similar, if not better, inhibitory effects. Control supernatant fluid from COS-7 cells transfected with vector alone actually promoted lymphoma cell growth. Accordingly, the inhibitory effects of CD40L on B lymphomas parallels that of antibodies to CD40.

EXAMPLE 4

This example illustrates the effect of anti-CD40 on the growth of human B-cell lymphomas in SCID mice. C.B-17 scid/scid (SCID) mice were obtained from the Animal Production Facility (NCI-FCRDC, Frederick, Md., USA) and were not used until 6–8 weeks of age. The mice were kept under specific-pathogen-free conditions at all times; they housed in microisolator cages, and all food, water and bedding were autoclaved before use. Trimethoprim/sulfamethoxazole (40 mg trimethoprim and 200 mg sulfamethoxazole per 320 ml) was included in suspension form in the drinking water given to the mice. All mice received antisera to asialo GM1 (Wako Chemical, Dallas, Tex., USA), a marker present on murine NK cells (Murphy et al., *Eur. J. Immunol.* 22:1421; 1992) intravenously one day before cell transfer, to remove host resistance to the tumor.

On day 0, SCID mice were injected either intravenously or intraperitoneally with $5 \times 10^6$ RL or TU2C cells. The tumor cell recipients then received either 2 µg of anti-CD40, or msIgG in 0.2 ml HBSS (Hank's balanced salt solution) intravenously every other day for a period of 10 days (total of 5 injections), starting at day 0, 3, or 14. Mice were monitored for tumor development and progression; moribund mice were euthanized. All mice were necropsied for evidence of tumor. Liver, kidney and lymphoid organs were analyzed histologically for presence of tumor cells. Both parametric (student's t test) and non-parametric (Wilcoxan rank sum test) analyses were performed to determine if the groups differed significantly (p<0.05). All experiments had 3–10 mice per group, and were performed 2–3 times. The results are presented in Table 1 below.

TABLE 1

Effect of anti-CD40 administration on survival in tumor-bearing mice

| Experiment | Tumor (Route) | Treatment (Initiation) | No. of Mice | Mean Day of Death |
|---|---|---|---|---|
| 1 | RL (i.p.) | None | 3 | 34 ± 0 |
|   | RL (i.p.) | anti-CD40 (day 0) | 6 | >138 ± 26.5[a] |
|   | TU2C (i.p.) | None | 3 | 28 ± 0 |
|   | TU2C (i.p.) | anti-CD40 (day 0) | 6 | >76 ± 45.0[b] |

TABLE 1-continued

Effect of anti-CD40 administration on survival in tumor-bearing mice

| Experiment | Tumor (Route) | Treatment (Initiation) | No. of Mice | Mean Day of Death |
|---|---|---|---|---|
| 2 | TU2C (i.v.) | None | 6 | 30 ± 6.3 |
|  | TU2C (i.v.) | anti-CD40 (day 3) | 6 | >38 ± 2.6$^c$ |
|  | TU2C (i.v.) | anti-CD40 (day 14) | 6 | >32 ± 4.6$^c$ |
| 3 | RL (i.p.) | None | 6 | 39 ± 3.5 |
|  | RL (i.p.) | anti-CD40 (day 3) | 6 | >107 ± 21.9$^a$ |
|  | RL (i.p.) | anti-CD40 (day 14) | 6 | >79 ± 34.3$^d$ | a: No deaths due to tumor; all (6) mice surviving
b: Two deaths due to tumor, other (4 out of 6 mice) showing no evidence of tumor.
c: One of six recipient mice showing no evidence of disease.
d: Three deaths due to tumor; three mice surviving.

Anti-CD40 significantly ($p<0.05$) improved survival of mice receiving either RL or TU2C tumors when treatment was initiated on day 0, 3 or 14. When SCID mice were treated with anti-CD40 on day 0, no evidence of tumor was present in the mice receiving the RL B-cell lymphoma line after several months. However, some mice receiving the EBV lymphoma TU2C and anti-CD40 did develop tumor several weeks after cessation of anti-CD40 treatment.

Differential patterns of metastatic growth were observed for the different routes of tumor cell administration. Mice receiving the EBV-induced lymphomas i.p. developed peritoneal tumors with extensive metastases in the lymph nodes and liver, whereas mice receiving the lymphomas i.v. primarily developed renal metastases. Anti-CD40 was capable of significantly inhibiting tumor grown and promoting survival of recipient mice regardless of the route of tumor administration.

Treatment of tumor-bearing mice with anti-CD40 also resulted in significantly improved survival when treatment was initiated 3 or 4 days after tumor cell transfer, and even as late as 14 days. These results indicate that anti-CD40 treatment was also efficacious when treatment was initiated with relatively large and extensive tumor burdens (>1 cm$^3$) in the recipient mice.

EXAMPLE 5

This example illustrates the effect of anti-CD40 on the growth of tumors in SCID mice injected with PBL from EBV-seropositive individuals. SCID mice (described in Example 4 above) were given injections of recombinant human growth hormone (rhGH: Genentech, South San Franciso, Calif., USA), which has been demonstrated to promote EBV-lymphogensis in huPBL-SCID mice (Murphy et al., *Brain Behav. Immun.* 6:355; 1992), presumable due to promotion of human T-cell engraftment in treated mice (Murphy et al., *Proc. Natl. Acad. Sci. USA* 89:4481; 1992). T-cell engraftment appears to be essential for human B-cell lymphoma formation in the huPBL-SCID model (18). rhGH (10 μg in 0.2 ml HBSS) was given i.p. on day 0 and every other day until time of assay 4–8 weeks later. Human PBLs were obtained from healthy donors in leukopacks. Anti-asialo GM-1 was administered as described for Example 4.

Human PBL were obtained from healthy, EBV-seropositive donors in leukopacks. All donors were screened for antibodies to human immunodeficiency virus type 1 (HIV-1) and for hepatitis B surface antigen (HBsAg), and provided informed consent before donation. The PBL were purified by counter-current elutriation, and the lymphocyte fraction, containing >90% lymphocytes as assessed by flow cytometry, were obtained. The PBL ($1\times10^8$) were injected i.p. into recipient SCID mice on day 0.

Mice were treated with anti-CD40, anti-CD20, or with msIgG (2 μg/0.2 ml PBS) i.p. every other day for 20 days for a total of 10 injections. Table 2 presents results representative of three experiments with 5–8 mice per group.

TABLE 2

Effect of anti-CD40 administration of EBV-induced
B-cell lymphoma development in huPBL-SCID mice chimeras

| Experiment | Treatment | No. of Mice | Mean Day of Death | % Incidence of Lymphoma$^a$ |
|---|---|---|---|---|
| A | msIgG | 6 | 31.4 ± 3.9 | 100% |
|  | anti-CD40 | 6 | >50$^b$ | 0% |
| B | msIgG | 8 | 26.3 ± 2.1$^c$ | 87% |
|  | anti-CD40 | 8 | >55$^b$ | 0% |
| C | msIgG | 5 | 33.2 ± 1.2 | 100% |
|  | anti-CD40 | 5 | >53$^b$ | 0% |
|  | anti-CD20 | 5 | >53 | 0% | a: Mice were moribund with evidence of extensive tumor nodules in the peritoneal cavity and evidence of lymphoma by histological assessment.
b: Treatment with anti-CD40 resulted in no deaths due to lymphoma and no evidence of lymphoma when assayed 2–6 weeks after cessation of anti-CD40 treatment. Anti-CD40 or anti-CD20 significantly ($p < 0.001$) increased survival compared to control recipients.
c: One out of 8 mice surviving and showing no evidence of tumor.

The results demonstrated that treatment of huPBL-SCID chimeric mice with anti-CD40 at the time of huPBL transfer completely prevented the development of human B-cell lymphomas in the mice. Although anti-CD20 had no effect on the lymphomas in vitro, treatment of the huPBL-SCID chimeras with anti-CD20 also prevented the occurrence of lymphoma.

EXAMPLE 6

This example illustrates the effect of anti-CD40 on the engraftment of human T (HLA$^+$, CD3$^+$) and B (HLA$^+$, CD3$^-$) cells in SCID mice. huPBL-SCID mice chimeras were prepared as described in Example 5 above. Percentages of human T and B cells found in the peritoneal cavity were determined, and the human immunoglobulin in the serum quantitated by enzyme-linked immunosorbent assay (ELISA). Animals were also examined for the presence of lymphoma; those animal that evidenced lymphoma were moribund, with evidence of extensive tumor nodules in the peritoneal cavity. Mice were assayed 4–8 weeks after huPBL transfer, with all control (msIg) treated mice succumbing to EBV-induced B cell lymphoma at day 33.2±1.2.

Single cell suspensions of peritoneal cavity cells were obtained, and evaluated by flow cytometry (FACS). Staining was performed in the presence of 2% human AB serum (Gibco BRL, Grand Island, N.Y., USA) to saturate human and mouse Fc receptors. Reagents used in the FACS analysis were monoclonal anti human-HLA-ABC conjugated to fluorescein isothiocyanate (FITC; Olympus, Lake Success, N.Y., USA), and Leu4-biotinylated anti-CD3 (Becton-Dickinson, Mountain View, Calif., USA). After primary antibody incubation, cells were analyzed using an EPICS flow cytometer.

Human immunoglobulin levels were assayed by ELISA. Flat-bottom 96-well microtiter plates (Coming Glass Works, Corning, N.Y., USA) were coated with goat anti-human Ig (Kirkegaard and Perry Laboratory, Gaithersburg, Md., USA) at 1 µg/ml in PBS, washed twice and blocked with 5% goat serum. The wells were then incubated with sera obtained from the huPBL-SCID mice chimeras, or a titration of human IgM+IgG standard (DAKO Corp., Santa Barbara, Calif., USA). After washing four times, alkaline phosphatase-conjugated goat anti-human Ig (Kirkegaard and Perry Laboratory, Gaithersburg, Md., USA) was added. The plates were incubated, and washed again. After the final wash, substrate was added, and the enzyme reaction allowed to develop. OD was measured at 402 nm. Results are presented in Table 3.

were treated with either anti-CD40 or anti-CD20, and percentages of human T and B cells found in the peritoneal cavity were determined, and the amount of human immunoglobulin in the serum quantitated as described in Example 6. Results are shown in Table 5.

TABLE 3

Effect of anti-CD40 on human B-cell engraftment and EBV-induced development in huPBL-SCID chimera mice

| Experiment | Animal No. | Treatment | # Peritoneal Cells (× $10^6$) | % cells $HLA^+$, $CD3^-$ | % cells $HLA^+$, $CD3^+$ | Human serum Ig (µg/ml) | Presence of Lymphoma |
|---|---|---|---|---|---|---|---|
| A | 1 | msIgG | 1.6 | 1.8 | 10.3 | 90 | + |
|   | 2 | msIgG | 1.4 | 0.8 | 2.8 | 120 | + |
|   | 3 | msIgG | 1.1 | 0.6 | 0.4 | 155 | + |
|   | 4 | msIgG | 1.5 | 0.6 | 1.4 | 406 | + |
|   | 5 | msIgG | 0.6 | 2.3 | 10.7 | 500 | + |
|   | 6 | anti-CD40 | 0.8 | 2.8 | 6.1 | 2.7 | − |
|   | 7 | anti-CD40 | 1.4 | 1.0 | 1.1 | 0.8 | − |
|   | 8 | anti-CD40 | 1.8 | 2.7 | 5.2 | 2.7 | − |
|   | 9 | anti-CD40 | 1.4 | 6.1 | 10.5 | 5.0 | − |
|   | 10 | anti-CD40 | 1.2 | 2.0 | 5.2 | 0.2 | − |
| B | 1 | anti-CD40 | 9.0 | 6.1 | 7.2 | 11.7 | − |
|   | 2 | anti-CD40 | 2.1 | 0.3 | 0.9 | 1.0 | − |
|   | 3 | anti-CD40 | 1.8 | 0.5 | 6.7 | 15.0 | − |
|   | 4 | anti-CD40 | 0.6 | 5.1 | 5.0 | 4.0 | − |
|   | 5 | anti-CD40 | 2.0 | 0.9 | 2.4 | 5.0 | − |
| C | 1 | anti-CD20 | 0.8 | 0.0 | 8.1 | 6.5 | − |
|   | 2 | anti-CD20 | 1.4 | 0.0 | 1.1 | 10.3 | − |
|   | 3 | anti-CD20 | 1.8 | 0.0 | 5.2 | 4.8 | − |
|   | 4 | anti-CD20 | 1.4 | 0.0 | 0.8 | 7.9 | − |
|   | 5 | anti-CD40 | 1.2 | 10.3 | 0.0 | 412.0 | − |
|   | 6 | anti-CD40 | 9.0 | 1.5 | 0.0 | 86.4 | − |
|   | 7 | anti-CD40 | 2.1 | 5.1 | 22.9 | 1110.0 | − |
|   | 8 | anti-CD40 | 1.8 | 0.6 | 0.9 | 18.5 | − |

Treatment with anti-CD40 did not prevent the engraftment of human T and B cells, as determined by FACS analysis of peritoneal cells, and determination of serum levels of human immunoglobulin. In Experiment A, the extent of human cell engraftment appeared quantitatively less in anti-CD40 treated animals than in animals receiving msIgG, based on the levels of human Ig in the serum. However, since the huPBL-SCID chimeric mice that did not receive anti-CD40 developed B-cell lymphomas, the high levels of human immunoglobulin detected are likely to be due to the B-cell lymphoma. In contrast to anti-CD40, treatment with anti-CD20 appeared to inhibit engraftment of B cells, both as indicated in lower percentages of B cells and in decreased levels of human Ig in the serum.

EXAMPLE 7

This example illustrates the effect of anti-CD40 and msIgG on the engraftment of B cells in SCID mice. huPBL-SCID mice chimeras were prepared as described in Example 5 above, except that the PBLs were obtained from EBV-negative donors. The chimeras were thus not expected to develop lymphomas, thereby providing a more accurate indication of engraftment of normal B cells. The chimeras

TABLE 5

Effect of Anti-CD40 Treatment on Human Immunoglobulin Production in huPBL-SCID Chimeras

| Animal # | Treatment[a] | Serum Immunoglobulin (µg/ml) |
|---|---|---|
| 1. | huPBL, msIgG | 125.0 |
| 2. | huPBL, msIgG | 150.0 |
| 3. | huPBL, msIgG | 1.7 |
| 4. | huPBL, msIgG | 94.0 |
| 5. | huPBL, msIgG | 112.0 |
| 6. | huPBL, msIgG | 18.8 |
| 7. | huPBL, anti-CD40 | 194.0 |
| 8. | huPBL, anti-CD40 | 269.0 |
| 9. | huPBL, anti-CD40 | 239.0 |
| 10. | huPBL, anti-CD40 | 119.0 |
| 11. | huPBL, anti-CD40 | 206.0 |
| 12. | huPBL, anti-CD40 | 150.0 | a: SCID mice received 100 million huPBL i.p. with 2 µg of anti-CD40 or msIgG given i.p. every other day for 20 days. Mice were analyzed for serum immunoglobulin levels using a human immunoglobulin-specific ELISA 3–4 weeks after huPBL transfer.

Treatment with anti-CD40 did promote engraftment of human B cells, indicating that anti-CD40 has additional value for treatment or prevention of lymphomas due to its ability to remove lymphoma cells while sparing normal B cells.

EXAMPLE 8

This example illustrates the effect of antibodies to CD40 on the growth of human melanoma cells in vitro. Antibody to CD40 ligand (M2) was tested in a proliferation assay substantially as described above, in Example 2, using M16 human melanoma cells, which express CD40.

Figure 5:
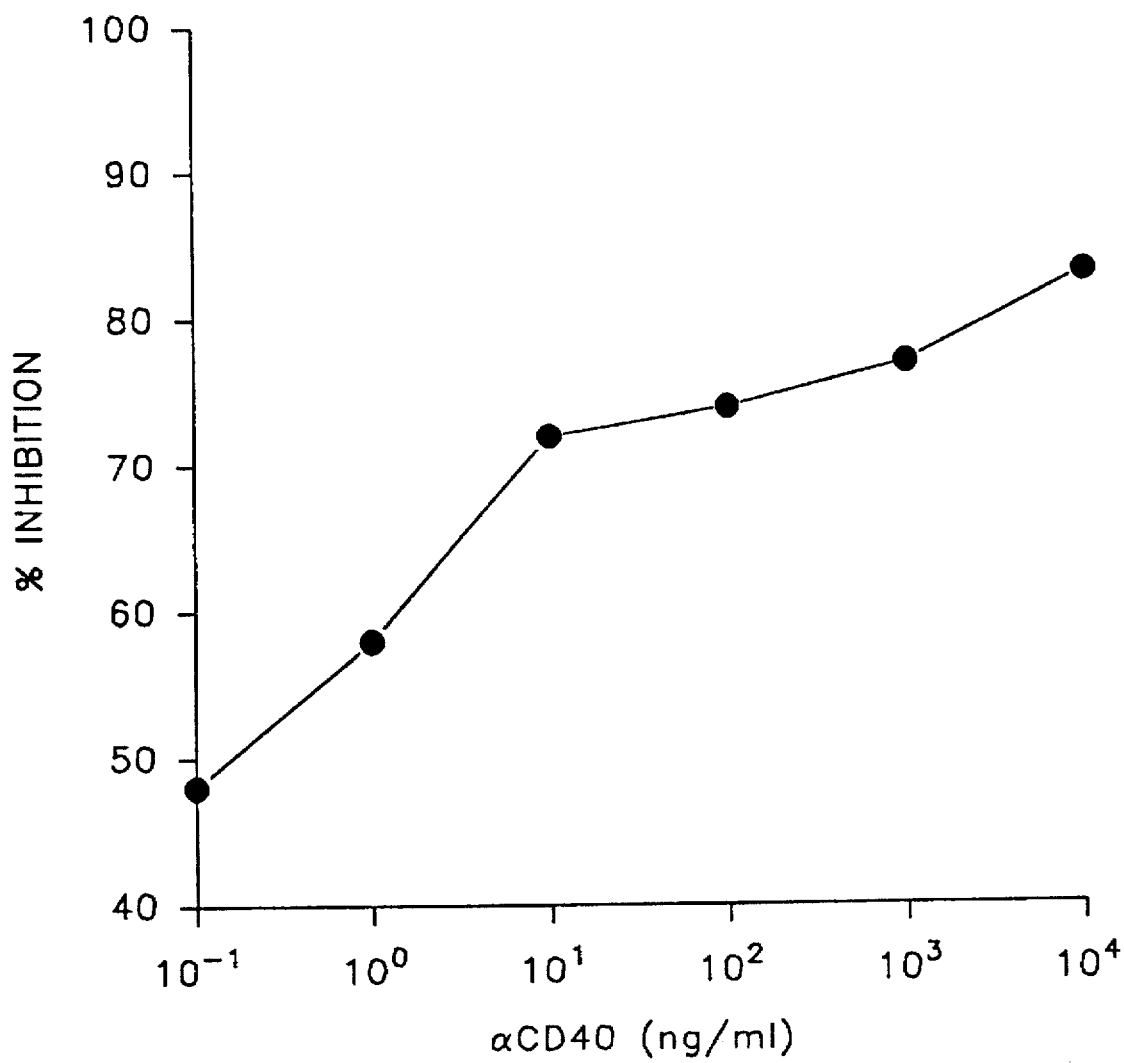
FIG. 5 shows that antibodies to CD40 inhibit the growth of human melanoma cells in vitro.

The results obtained are presented in FIG. 5; values are presented as percent of inhibition compared to control supernatant fluids. Incubation with anti-CD40 monoclonal antibody M2 resulted in significant inhibition of the proliferation of M16 human melanoma cell line tested, with as little as 0.1 ng/ml causing inhibition of almost 50%. Increased inhibition was observed with increasing concentration of anti-CD40.

EXAMPLE 9

This example illustrates the effect of recombinant human CD40 ligand on the growth of human B-cell lymphomas in SCID mice. SCID mice were obtained, and treated substantially as described in Example 4, above. On day 0, SCID mice were injected either intraperitoneally with $5\times10^6$ RL or TU2C cells. The tumor cell recipients then received 100 µl of concentrated supernatant fluid from cells transfected with either a vector encoding human CD40 ligand, or vector alone (control). Two concentrations of the CD40 ligand-containing supernatant fluid were tested: a ten-fold concentrate and a two-fold concentrate (10x and 2x, respectively). The concentrated supernatants were administered intraperitoneally every third day for a period of 15 days (total of 5 injections), starting at day 3. Mice were monitored for tumor development and progression; moribund mice were euthanized. All mice were necropsied for evidence of tumor. Liver, kidney and lymphoid organs were analyzed histologically for presence of tumor cells. Both parametric (student's t test) and non-parametric (Wilcoxan rank sum test) analyses were performed to determine if the groups differed significantly ($p<0.05$). All experiments had 7–10 mice per group, and were performed 3 times.

Figure 6:
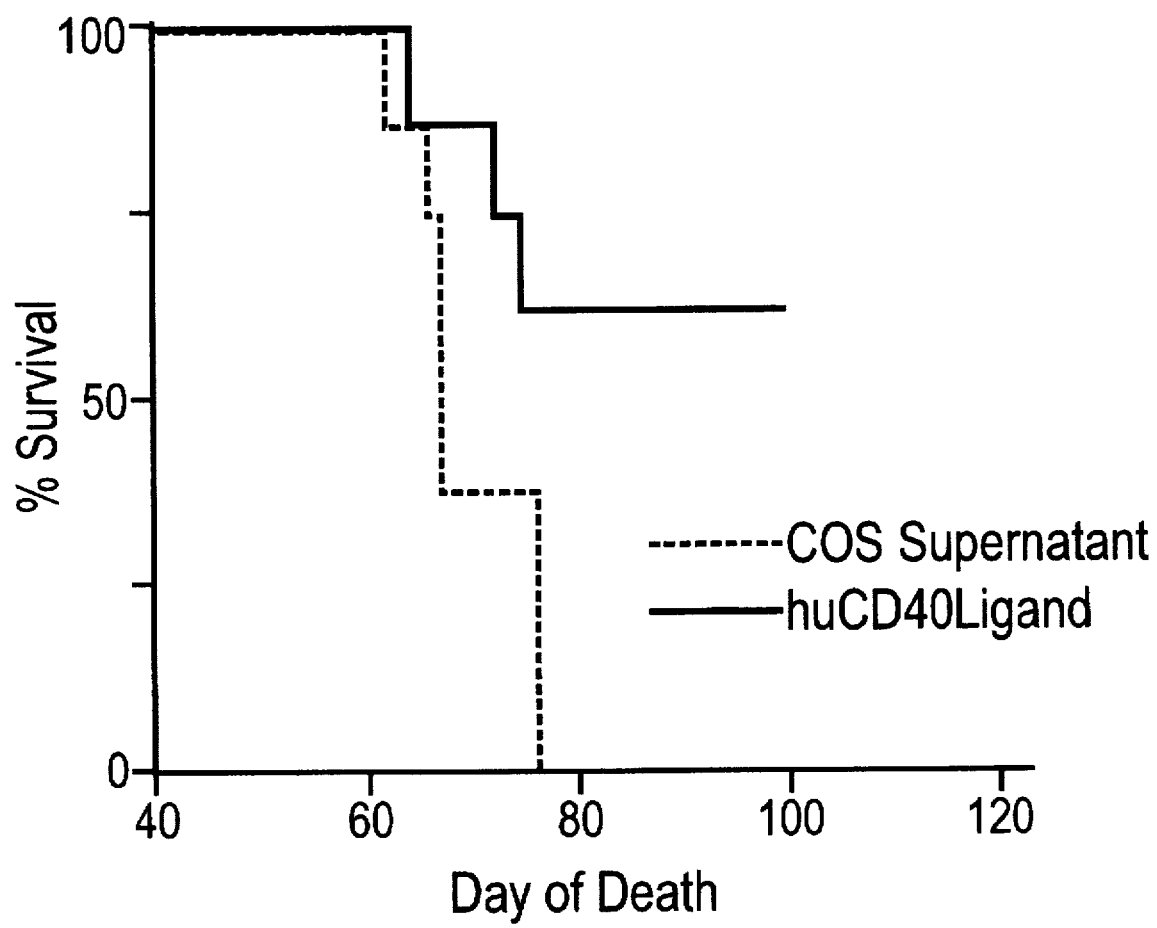
FIG. 6 demonstrates the ability of soluble CD40 ligand to inhibit the growth of B-cell lymphomas in vivo.

The results of an exemplary experiment utilizing RL cells are shown in FIG. 6. Similar to the results obtained in vitro in Example 3, recombinant CD40 ligand inhibited the growth of tumor cells in vivo in SCID mice.

---

What is claimed is:

1. A method of treating a mammal afflicted with a disease characterized by neoplastic cells that express CD40, comprising administering a therapeutically effective amount of a CD40 binding protein capable of binding CD40 and inhibiting binding of CD40 to CD40L, as determined by observing at least about 90% inhibition of the binding of soluble CD40 to CD40L, in a pharmaceutically acceptable buffer, wherein said CD40 binding protein is selected from the group consisting of monoclonal antibodies to CD40, CD40 ligand and combinations thereof, and wherein the therapeutically effective amount is from about 0.01 to about 1 mg/kg body weight and inhibits proliferation of the neoplastic cells.

2. The method of claim 1, wherein the CD40 binding protein is selected from the group consisting of monoclonal antibody HuCD40-M2 (ATCC HB11459) and CD40 binding proteins comprising an antigen binding domain derived from antibody HuCD40-M2.

3. The method of claim 1, wherein the CD40-binding protein is soluble, oligomeric CD40 ligand comprising a CD40-binding peptide and an oligomer-forming peptide wherein said CD40-binding protein is encoded by a DNA selected from the group consisting of:

(a) nucleotides 184 through 828, 193 through 828, 193 through 762, or 403 through 762 of the DNA sequence set forth in SEQ ID NO:1;

(b) DNA sequences which hybridize to a DNA sequence of (a) or its complement under conditions of severe stringency (hybridization in 6 X SSC at 63° C. overnight; washing in 3 X SSC at 55° C.) and which encode CD40L that binds CD40 and inhibits binding of CD40 to CD40L, as determined by observing at least about 90% inhibition of the binding of soluble CD40 to CD40L;

(c) DNA sequences which encode fragments of the extracellular domain of CD40L that bind CD40 and inhibit binding of CD40 to CD40L, as determined by observing at least about 90% inhibition of the binding of soluble CD40 to CD40L, and (d) DNA sequences which, due to the degeneracy of the genetic code, encode CD40L polypeptides encoded by any of the foregoing DNA sequences and their complements.

4. The method of claim 3, wherein the oligomer-forming peptide is selected from the group consisting of an immunoglobulin Fc domain and an oligomerizing leucine zipper domain.

5. The method of claim 4, wherein the oligomerizing leucine zipper domain forms a trimer in solution.

6. The method of claim 1, wherein the cells expressing CD40 are selected from the group consisting of B lymphoma cells, melanoma cells and carcinoma cells.

7. The method of claim 3, whereto the cells expressing, CD40 are selected from the group consisting of B lymphoma cells, melanoma cells and carcinoma cells.

8. The method of claim 4, wherein the cells expressing CD40 are selected from the group consisting of B lymphoma cells, melanoma cells and carcinoma cells.

9. The method of claim 5, wherein the cells expressing CD40 are selected from the group consisting of B lymphoma cells, melanoma cells and carcinoma cells.

10. A method of preventing a disease characterized by neoplastic cells that express CD40, in a mammal susceptible to the disease, comprising administering a therapeutically effective amount of a CD40 binding protein capable of binding CD40 and inhibiting binding of CD40 to CD40L, as determined by observing at least about 90% inhibition of the binding of soluble CD40 to CD40L, in a pharmaceutically acceptable buffer, wherein the therapeutically effective amount is from about 0.01 to about 1 mg/kg body weight and inhibits proliferation of the neoplastic cells.

11. The method of claim 10, wherein the CD40 binding protein is selected from the group consisting of monoclonal antibody HuCD40-M2 (ATCC HB 11459) and CD40 binding proteins comprising an antigen binding domain derived from antibody HuCD40-M2.

12. The method of claim 10, wherein the CD40-binding protein is soluble, oligomeric CD40 ligand comprising a CD40-binding peptide and an oligomer-forming peptide wherein said CD40-binding protein is encoded by a DNA selected from the group consisting of:

(a) nucleotides 184 through 828, 193 through 828, 193 through 762, or 403 through 762 of the DNA sequence set forth in SEQ ID NO:1;

(b) DNA sequences which hybridize to a DNA sequence of (a) or its complement under conditions of severe stringency (hybridization in 6 X SSC at 63° C. overnight; washing in 3 X SSC at 55° C.) and which encode CD40L that binds CD40 and inhibits binding of CD40 to CD40L, as determined by observing at least about 90% inhibition of the binding of soluble CD40 to CD40L;

(c) DNA sequences which encode fragments of the extracellular domain of CD40L that bind CD40 and inhibit binding of CD40 to CD40L, as determined by observing at least about 90% inhibition of the binding of soluble CD40 to CD40L, and (d) DNA sequences which, due to the degeneracy of the genetic code, encode CD40L polypeptides encoded by any of the foregoing DNA sequences and their complements.

13. The method of claim 12, wherein the oligomer-forming peptide is selected from the group consisting of an immunoglobulin Fc domain and an oligomerizing leucine zipper domain.

14. The method of claim 13, wherein the oligomerizing leucine zipper domain forms a trimer in solution.

15. The method of claim 5, wherein the oligomerizing leucine zipper domain is selected from the group consisting of:

(a) a peptide having an amino acid sequence represented by SEQ ID NO:4; and (b) a peptide according to (a) in which conservative amino acid substitutions have been made, wherein the peptide is capable of forming an oligomeric CD40L fusion protein.

16. The method of claim 9, wherein the oligomerizing leucine zipper domain is selected from the group consisting of:

(a) a peptide having an amino acid sequence represented by SEQ ID NO:4; and (b) a peptide according to (a) in which conservative amino acid substitutions have been made, wherein the peptide is capable of forming an oligomeric CD40L fusion protein.

17. The method of claim 14, wherein the oligomerizing leucine zipper domain is selected from the group consisting of:

(a) a peptide having an amino acid sequence represented by SEQ ID NO:4; and (b) a peptide according to (a) in which conservative amino acid substitutions have been made, wherein the peptide is capable of forming an oligomeric CD40L fusion protein.

18. The method of claim 2, wherein the cells expressing CD40 are selected from the group consisting of B lymphoma cells, melanoma cells and carcinoma cells.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 840 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens ( v i i ) IMMEDIATE SOURCE:
        ( B ) CLONE: CD40-L ( i x ) FEATURE:
        ( A ) NAME/KEY: CDS
        ( B ) LOCATION: 46..831

( x i ) SEQUENCE DESCRIPTION: SEQ ID NO:1:

```
TGCCACCTTC TCTGCCAGAA GATACCATTT CAACTTTAAC ACAGC ATG ATC GAA          54
                                                 Met Ile Glu
                                                  1

ACA TAC AAC CAA ACT TCT CCC CGA TCT GCG GCC ACT GGA CTG CCC ATC      102
Thr Tyr Asn Gln Thr Ser Pro Arg Ser Ala Ala Thr Gly Leu Pro Ile
     5                  10                  15

AGC ATG AAA ATT TTT ATG TAT TTA CTT ACT GTT TTT CTT ATC ACC CAG      150
Ser Met Lys Ile Phe Met Tyr Leu Leu Thr Val Phe Leu Ile Thr Gln
 20                  25                  30                  35

ATG ATT GGG TCA GCA CTT TTT GCT GTG TAT CTT CAT AGA AGG TTG GAC      198
Met Ile Gly Ser Ala Leu Phe Ala Val Tyr Leu His Arg Arg Leu Asp
                 40                  45                  50
```

| | | | | | | | | | | | | | | | | |
|---|---|---|---|---|---|---|---|---|---|---|---|---|---|---|---|---|
| AAG | ATA | GAA | GAT | GAA | AGG | AAT | CTT | CAT | GAA | GAT | TTT | GTA | TTC | ATG | AAA | 246 |
| Lys | Ile | Glu | Asp 55 | Glu | Arg | Asn | Leu | His 60 | Glu | Asp | Phe | Val | Phe 65 | Met | Lys | |
| ACG | ATA | CAG | AGA | TGC | AAC | ACA | GGA | GAA | AGA | TCC | TTA | TCC | TTA | CTG | AAC | 294 |
| Thr | Ile | Gln 70 | Arg | Cys | Asn | Thr | Gly 75 | Glu | Arg | Ser | Leu | Ser 80 | Leu | Leu | Asn | |
| TGT | GAG | GAG | ATT | AAA | AGC | CAG | TTT | GAA | GGC | TTT | GTG | AAG | GAT | ATA | ATG | 342 |
| Cys | Glu 85 | Glu | Ile | Lys | Ser | Gln 90 | Phe | Glu | Gly | Phe | Val 95 | Lys | Asp | Ile | Met | |
| TTA | AAC | AAA | GAG | GAG | ACG | AAG | AAA | GAA | AAC | AGC | TTT | GAA | ATG | CAA | AAA | 390 |
| Leu 100 | Asn | Lys | Glu | Glu | Thr 105 | Lys | Lys | Glu | Asn | Ser 110 | Phe | Glu | Met | Gln | Lys 115 | |
| GGT | GAT | CAG | AAT | CCT | CAA | ATT | GCG | GCA | CAT | GTC | ATA | AGT | GAG | GCC | AGC | 438 |
| Gly | Asp | Gln | Asn | Pro 120 | Gln | Ile | Ala | Ala | His 125 | Val | Ile | Ser | Glu | Ala 130 | Ser | |
| AGT | AAA | ACA | ACA | TCT | GTG | TTA | CAG | TGG | GCT | GAA | AAA | GGA | TAC | TAC | ACC | 486 |
| Ser | Lys | Thr | Thr 135 | Ser | Val | Leu | Gln | Trp 140 | Ala | Glu | Lys | Gly | Tyr 145 | Tyr | Thr | |
| ATG | AGC | AAC | AAC | TTG | GTA | ACC | CTG | GAA | AAT | GGG | AAA | CAG | CTG | ACC | GTT | 534 |
| Met | Ser | Asn 150 | Asn | Leu | Val | Thr | Leu 155 | Glu | Asn | Gly | Lys | Gln 160 | Leu | Thr | Val | |
| AAA | AGA | CAA | GGA | CTC | TAT | TAT | ATC | TAT | GCC | CAA | GTC | ACC | TTC | TGT | TCC | 582 |
| Lys | Arg 165 | Gln | Gly | Leu | Tyr | Tyr 170 | Ile | Tyr | Ala | Gln | Val 175 | Thr | Phe | Cys | Ser | |
| AAT | CGG | GAA | GCT | TCG | AGT | CAA | GCT | CCA | TTT | ATA | GCC | AGC | CTC | TGC | CTA | 630 |
| Asn 180 | Arg | Glu | Ala | Ser | Ser 185 | Gln | Ala | Pro | Phe | Ile 190 | Ala | Ser | Leu | Cys | Leu 195 | |
| AAG | TCC | CCC | GGT | AGA | TTC | GAG | AGA | ATC | TTA | CTC | AGA | GCT | GCA | AAT | ACC | 678 |
| Lys | Ser | Pro | Gly | Arg 200 | Phe | Glu | Arg | Ile | Leu 205 | Leu | Arg | Ala | Ala | Asn 210 | Thr | |
| CAC | AGT | TCC | GCC | AAA | CCT | TGC | GGG | CAA | CAA | TCC | ATT | CAC | TTG | GGA | GGA | 726 |
| His | Ser | Ser | Ala 215 | Lys | Pro | Cys | Gly | Gln 220 | Gln | Ser | Ile | His | Leu 225 | Gly | Gly | |
| GTA | TTT | GAA | TTG | CAA | CCA | GGT | GCT | TCG | GTG | TTT | GTC | AAT | GTG | ACT | GAT | 774 |
| Val | Phe | Glu 230 | Leu | Gln | Pro | Gly | Ala 235 | Ser | Val | Phe | Val | Asn 240 | Val | Thr | Asp | |
| CCA | AGC | CAA | GTG | AGC | CAT | GGC | ACT | GGC | TTC | ACG | TCC | TTT | GGC | TTA | CTC | 822 |
| Pro | Ser | Gln 245 | Val | Ser | His | Gly | Thr 250 | Gly | Phe | Thr | Ser | Phe 255 | Gly | Leu | Leu | |
| AAA | CTC | TGAACAGTGT | CA | | | | | | | | | | | | | 840 |
| Lys 260 | Leu | | | | | | | | | | | | | | | |

( 2 ) INFORMATION FOR SEQ ID NO:2:

( i ) SEQUENCE CHARACTERISTICS:
        ( A ) LENGTH: 261 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met 1 | Ile | Glu | Thr | Tyr 5 | Asn | Gln | Thr | Ser | Pro 10 | Arg | Ser | Ala | Ala | Thr 15 | Gly |
| Leu | Pro | Ile | Ser 20 | Met | Lys | Ile | Phe | Met 25 | Tyr | Leu | Leu | Thr | Val 30 | Phe | Leu |
| Ile | Thr | Gln 35 | Met | Ile | Gly | Ser | Ala 40 | Leu | Phe | Ala | Val | Tyr 45 | Leu | His | Arg |
| Arg | Leu 50 | Asp | Lys | Ile | Glu | Asp 55 | Glu | Arg | Asn | Leu | His 60 | Glu | Asp | Phe | Val |

| Phe | Met | Lys | Thr | Ile | Gln | Arg | Cys | Asn | Thr | Gly | Glu | Arg | Ser | Leu | Ser |
|65|||||70|||||75|||||80|

| Leu | Leu | Asn | Cys | Glu | Glu | Ile | Lys | Ser | Gln | Phe | Glu | Gly | Phe | Val | Lys |
|||||85|||||90|||||95||

| Asp | Ile | Met | Leu | Asn | Lys | Glu | Glu | Thr | Lys | Lys | Glu | Asn | Ser | Phe | Glu |
||||100|||||105|||||110|||

| Met | Gln | Lys | Gly | Asp | Gln | Asn | Pro | Gln | Ile | Ala | Ala | His | Val | Ile | Ser |
|||115|||||120|||||125||||

| Glu | Ala | Ser | Ser | Lys | Thr | Thr | Ser | Val | Leu | Gln | Trp | Ala | Glu | Lys | Gly |
||130|||||135|||||140|||||

| Tyr | Tyr | Thr | Met | Ser | Asn | Asn | Leu | Val | Thr | Leu | Glu | Asn | Gly | Lys | Gln |
|145|||||150|||||155|||||160|

| Leu | Thr | Val | Lys | Arg | Gln | Gly | Leu | Tyr | Tyr | Ile | Tyr | Ala | Gln | Val | Thr |
|||||165|||||170|||||175||

| Phe | Cys | Ser | Asn | Arg | Glu | Ala | Ser | Ser | Gln | Ala | Pro | Phe | Ile | Ala | Ser |
||||180|||||185|||||190|||

| Leu | Cys | Leu | Lys | Ser | Pro | Gly | Arg | Phe | Glu | Arg | Ile | Leu | Leu | Arg | Ala |
|||195|||||200|||||205||||

| Ala | Asn | Thr | His | Ser | Ser | Ala | Lys | Pro | Cys | Gly | Gln | Gln | Ser | Ile | His |
||210|||||215|||||220|||||

| Leu | Gly | Gly | Val | Phe | Glu | Leu | Gln | Pro | Gly | Ala | Ser | Val | Phe | Val | Asn |
|225|||||230|||||235|||||240|

| Val | Thr | Asp | Pro | Ser | Gln | Val | Ser | His | Gly | Thr | Gly | Phe | Thr | Ser | Phe |
|||||245|||||250|||||255||

| Gly | Leu | Leu | Lys | Leu |
||||260||

( 2 ) INFORMATION FOR SEQ ID NO:3:

( i ) SEQUENCE CHARACTERISTICS:
        ( A ) LENGTH: 740 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: HUMAN ( v i i ) IMMEDIATE SOURCE:
        ( B ) CLONE: IgG1 Fc ( x i ) SEQUENCE DESCRIPTION: SEQ ID NO:3:

| | | | | | | |
|---|---|---|---|---|---|---|
| CGGTACCGCT | AGCGTCGACA | GGCCTAGGAT | ATCGATACGT | AGAGCCCAGA | TCTTGTGACA | 60 |
| AAACTCACAC | ATGCCCACCG | TGCCCAGCAC | CTGAACTCCT | GGGGGGACCG | TCAGTCTTCC | 120 |
| TCTTCCCCCC | AAAACCCAAG | GACACCCTCA | TGATCTCCCG | GACCCCTGAG | GTCACATGCG | 180 |
| TGGTGGTGGA | CGTGAGCCAC | GAAGACCCTG | AGGTCAAGTT | CAACTGGTAC | GTGGACGGCG | 240 |
| TGGAGGTGCA | TAATGCCAAG | ACAAAGCCGC | GGGAGGAGCA | GTACAACAGC | ACGTACCGGG | 300 |
| TGGTCAGCGT | CCTCACCGTC | CTGCACCAGG | ACTGGCTGAA | TGGCAAGGAC | TACAAGTGCA | 360 |
| AGGTCTCCAA | CAAAGCCCTC | CCAGCCCCCA | TGCAGAAAAC | CATCTCCAAA | GCCAAAGGGC | 420 |
| AGCCCCGAGA | ACCACAGGTG | TACACCCTGC | CCCCATCCCG | GGATGAGCTG | ACCAAGAACC | 480 |
| AGGTCAGCCT | GACCTGCCTG | GTCAAAGGCT | TCTATCCCAG | CGACATCGCC | GTGGAGTGGG | 540 |

-continued

```
AGAGCAATGG  GCAGCCGGAG  AACAACTACA  AGACCACGCC  TCCCGTGCTG  GACTCCGACG      600

GCTCCTTCTT  CCTCTACAGC  AAGCTCACCG  TGGACAAGAG  CAGGTGGCAG  CAGGGGAACG      660

TCTTCTCATG  CTCCGTGATG  CATGAGGCTC  TGCACAACCA  CTACACGCAG  AAGAGCCTCT      720

CCCTGTCTCC  GGGTAAATGA                                                     740
```

( 2 ) INFORMATION FOR SEQ ID NO:4:

( i ) SEQUENCE CHARACTERISTICS:
        ( A ) LENGTH: 33 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

```
Arg  Met  Lys  Gln  Ile  Glu  Asp  Lys  Ile  Glu  Glu  Ile  Leu  Ser  Lys  Ile
1                  5                       10                      15

Tyr  His  Ile  Glu  Asn  Glu  Ile  Ala  Arg  Ile  Lys  Lys  Leu  Ile  Gly  Glu
              20                      25                      30

Arg
```